United States Patent
Karki et al.

(10) Patent No.: US 11,197,842 B2
(45) Date of Patent: Dec. 14, 2021

(54) PHARMACEUTICAL BEAD FORMULATIONS COMPRISING DIMETHYL FUMARATE

(71) Applicant: BIOGEN MA INC., Cambridge, MA (US)

(72) Inventors: Shyam B. Karki, Hillsborough, NJ (US); Peter Zawaneh, Brookline, MA (US); Cheuk-Yui Leung, Acton, MA (US); Kalyan Vasudevan, Cambridge, MA (US); Yiqing Lin, Lexington, MA (US); Jin Xu, Waltham, MA (US); Andrea Trementozzi, Sherborn, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 15/527,531

(22) PCT Filed: Nov. 19, 2015

(86) PCT No.: PCT/US2015/061456
§ 371 (c)(1),
(2) Date: May 17, 2017

(87) PCT Pub. No.: WO2016/081676
PCT Pub. Date: May 26, 2016

(65) Prior Publication Data
US 2018/0153845 A1 Jun. 7, 2018

Related U.S. Application Data

(60) Provisional application No. 62/081,889, filed on Nov. 19, 2014.

(51) Int. Cl.
*A61K 31/225* (2006.01)
*A61P 37/00* (2006.01)
*A61K 9/16* (2006.01)
*A61K 9/24* (2006.01)
*A61K 9/28* (2006.01)
*A61K 9/50* (2006.01)
*A61P 25/00* (2006.01)

(52) U.S. Cl.
CPC .......... *A61K 31/225* (2013.01); *A61K 9/1676* (2013.01); *A61K 9/209* (2013.01); *A61K 9/288* (2013.01); *A61K 9/2826* (2013.01); *A61K 9/2846* (2013.01); *A61K 9/2853* (2013.01); *A61K 9/2866* (2013.01); *A61K 9/2873* (2013.01); *A61K 9/2886* (2013.01); *A61K 9/5078* (2013.01); *A61P 25/00* (2018.01); *A61P 37/00* (2018.01)

(58) Field of Classification Search
None
See application file for complete search history.

(56) References Cited

U.S. PATENT DOCUMENTS

| 5,213,811 | A | 5/1993 | Frisbee et al. | |
| 6,737,082 | B1* | 5/2004 | Picornell Darder | A61K 9/1676 424/490 |
| 2002/0155156 | A1* | 10/2002 | Mulye | A61K 9/2826 424/482 |
| 2006/0193914 | A1* | 8/2006 | Ashworth | A61K 9/2031 424/469 |
| 2012/0065221 | A1* | 3/2012 | Babul | A61K 9/2086 514/289 |
| 2013/0216615 | A1* | 8/2013 | Goldman | A61K 31/616 424/451 |
| 2014/0037740 | A1* | 2/2014 | Nilsson | A61K 9/14 424/490 |
| 2014/0171504 | A1 | 6/2014 | Ganapathy | |
| 2014/0275250 | A1 | 9/2014 | Cundy | |

FOREIGN PATENT DOCUMENTS

| CN | 104027311 A | 9/2014 |
| WO | 2005034916 A1 | 4/2005 |
| WO | 2006024479 A2 | 3/2006 |
| WO | 2010/079221 A1 | 7/2010 |
| WO | 2010/079222 A1 | 7/2010 |
| WO | 2011100589 A1 | 8/2011 |
| WO | 2013076216 A1 | 5/2013 |
| WO | 2013119677 A1 | 8/2013 |
| WO | WO-2013-119677 * | 8/2013 |
| WO | 2014020156 A1 | 2/2014 |
| WO | 2014143146 A1 | 9/2014 |

OTHER PUBLICATIONS

Cohen et al: "The Future of Multiple Sclerosis Treatment", Journal of Neurological Sciences, Elsevier Scientific Publishing Co., Amsterdam, NL, vol. 277, Feb. 1, 2009, pp. S55-S61.

* cited by examiner

*Primary Examiner* — Celeste A Roney
(74) *Attorney, Agent, or Firm* — McCarter & English, LLP; Steven G. Davis; Xin Zhang

(57) ABSTRACT

The present invention provides novel pharmaceutical compositions of dimethyl fumarate. The pharmaceutical compositions of the present invention are in the form of a bead and comprise (i) an inert core; (ii) a first layer surrounding the inert core, wherein the first layer comprises dimethyl fumarate; and (iii) an enteric coating surrounding the first layer. Also provided are pharmaceutical compositions in the form of a bead comprising a core and an enteric coating surrounding the core, wherein the core comprises dimethyl fumarate. Methods of using the pharmaceutical compositions of the present invention for treating multiple sclerosis are also included.

20 Claims, 7 Drawing Sheets

PHARMACEUTICAL BEAD FORMULATIONS COMPRISING DIMETHYL FUMARATE

REFERENCE TO RELATED APPLICATIONS

This application is a U.S. national stage filing under 35 U.S.C. § 371 based on International Application PCT/US2015/061456, filed Nov. 19, 2015, which claims the benefit of the filing date, under 35 U.S.C. § 119(e), of U.S. Provisional Application No. 62/081,889, filed on Nov. 19, 2014. The entire contents of each of the foregoing applications, including all drawings, formulae, specification, and claims, are incorporated herein by reference.

BACKGROUND OF THE INVENTION

Tecfidera® (dimethyl fumarate) was approved by FDA in March, 2013 to be used for treating adults with relapsing forms of multiple sclerosis (MS). The starting dose for the currently approved formulation of Tecfidera® is 120 mg twice a day orally. After 7 days, the dose is increased to the maintenance dose of 240 mg twice a day orally.

Dimethyl fumarate (DMF) quickly gets absorbed in vivo and converted to monomethyl fumarate (MMF). The half-life of MMF was shown to be approximately 1 hour (0.9 h in rat at 100 mg/Kg oral dose). Both DMF and MMF are metabolized by esterases which are ubiquitous in the GI tract, blood and tissues.

DMF has demonstrated an acceptable safety profile in phase 3 clinical trials. However, tolerability issues such as flushing and gastrointestinal events were observed. While these events are generally mild to moderate in severity, it is desirable to reduce these side effects. It is also desirable to develop a once a day dosing formulation as opposed to the current twice a day formulation to improve patient compliance and convenience.

As such, there is a need for new pharmaceutical formulations of dimethyl fumarate with improved pharmacokinetic profiles and/or dosing regimen and reduced side effects.

SUMMARY OF THE INVENTION

The present invention provides novel pharmaceutical compositions of dimethyl fumarate that have pharmacokinetic profiles suitable for a once daily dosing regimen. The pharmaceutical compositions of the present invention have AUC and/or $C_{max}$ that are comparable with the currently approved twice-a-day formulation. In addition, the pharmaceutical compositions of the present invention have a desirable extended release profile that may reduce the GI side effects observed for the current formulation. Moreover, the pharmacokinetic profiles show that the pharmaceutical compositions of the present invention have maximized absorption of dimethyl fumarate in vivo.

One aspect of the present invention is directed to a pharmaceutical composition in the form of a bead comprising:
  an inert core;
  a first layer surrounding the inert core, wherein the first layer comprises dimethyl fumarate; and
  an enteric coating surrounding the first layer.

In one embodiment, the pharmaceutical composition can further comprises a functional coating surrounding the enteric coating.

In another aspect, the present invention is directed to a pharmaceutical composition in the form of a bead comprising:
  an inert core;
  a first layer surrounding the inert core, wherein the first layer comprises dimethyl fumarate;
  a functional coating surrounding the first layer; and
  an enteric coating surrounding the functional coating.

In another aspect, the present invention is directed to a pharmaceutical composition in the form of a bead comprising:
  a core comprising dimethyl fumarate; and
  an enteric coating surrounding the core.

In one embodiment, the pharmaceutical composition can further comprises a functional coating surrounding the enteric coating.

In yet another aspect, the present invention is directed to a pharmaceutical composition in the form of a bead comprising:
  a core comprising dimethyl fumarate;
  a functional coating surrounding the core; and
  an enteric coating surrounding the functional coating.

In yet another aspect, the present invention provides a method of treating a subject having multiple sclerosis. The method comprises administering to the subject an effective amount of a pharmaceutical composition of the present invention described herein.

The present invention also provides a pharmaceutical composition described herein for use in treating a subject having multiple sclerosis.

Use of a pharmaceutical composition described herein for the manufacture of a medicament in treating multiple sclerosis is also included in the present invention.

DETAILED DESCRIPTION OF THE INVENTION

Figure 1:
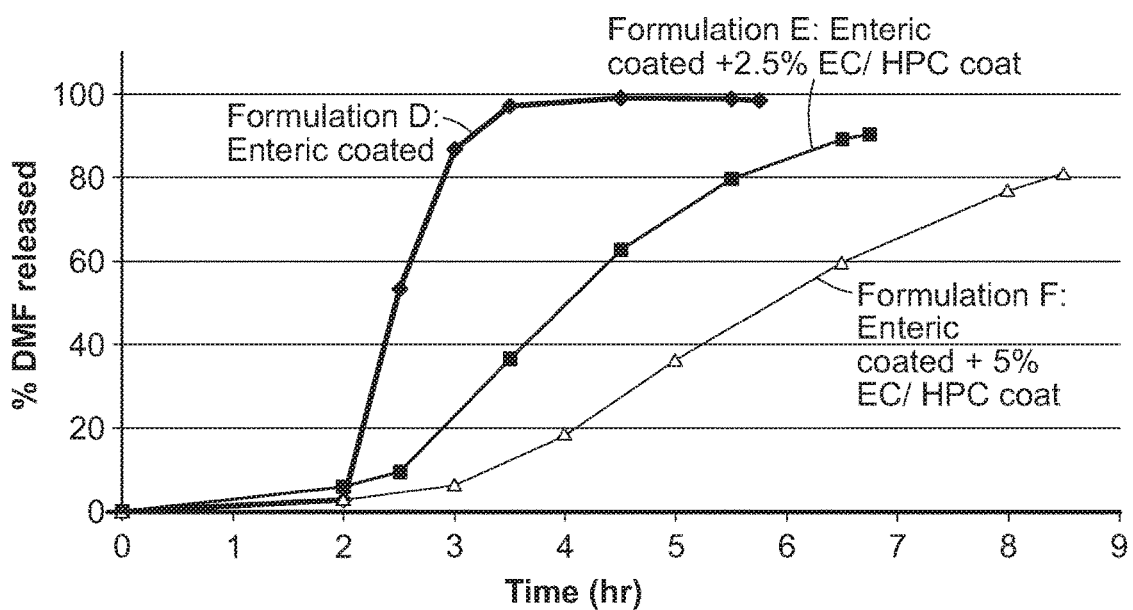
FIG. 1. shows in vitro dissolution profiles for formulations D, E and F of the present invention using dissolution test 1.

In a first embodiment, the present invention is directed to a pharmaceutical composition in the form of a bead comprising:
an inert core;
a first layer surrounding the inert core, wherein the first layer comprises dimethyl fumarate; and
an enteric coating surrounding the first layer.

In a second embodiment, the pharmaceutical composition described in the first embodiment can further comprises a functional coating surrounding the enteric coating.

In a third embodiment, the present invention is directed to a pharmaceutical composition in the form of a bead comprising:
an inert core;
a first layer surrounding the inert core, wherein the first layer comprises dimethyl fumarate;
a functional coating surrounding the first layer; and
an enteric coating surrounding the first functional coating.

As used herein, the term "inert core" refers to a core comprising material(s) that are unreactive towards the active substance and any components of the bead and/or have no effect on the biological activity of the active substance, i.e., dimethyl fumarate. In addition, the inert core does not contain any active substance. In certain embodiments, the inert core comprises a pharmaceutically acceptable inert material(s). Exemplary inert core materials include, but are not limited to, starch, dextrose, sucrose, lactose, maltose, and microcrystalline cellulose. In one embodiment, the inert core comprises lactose. In an alternative embodiment, the inert core comprises starch. In yet another alternative, the inert core comprises sucrose.

In certain embodiments, for the pharmaceutical compositions described in the first, second or third embodiment, the weight percentage for the inert core is 10%-60% or 20-40% of the total weight of the inert core and the first layer. More specifically, the weight percentage for the inert core is 30%-40% or 20-30% of the total weight of the inert core and the first layer. Even more specifically, the weight percentage for the inert core is 20-24% of the total weight of the inert core and the first layer.

In certain embodiments, for the pharmaceutical compositions described in the first, second or third embodiment, the inert core is a sphere having a diameter of 200-850 µm. More specifically, the sphere has a diameter of 250-350 µm, 300-400 µm, 500-600 µm or 700-850 µm. Even more specifically, the sphere has a diameter of 350 µm, 550 µm or 750 µm.

In certain embodiment, for the pharmaceutical compositions described in the first, second or third embodiment, the beads have a diameter of 0.5-2 mm, 0.5-1.5 mm, 0.8-2 mm, 0.8-1.5 mm, 1-2 mm or 1-1.5 mm. More specifically, the beads have a diameter of 0.9-1.5 mm, 0.9-1.4 mm, 0.9-1.3 mm, 0.9-1.2 mm, 1-1.4 mm, 1-1.3 mm or 1-1.2 mm.

In certain embodiments, for the pharmaceutical compositions described in the first, second or third embodiment, the active substance dimethyl fumarate is layered on the inert core. More specifically, dimethyl fumarate is layered on the inert core by spraying a solution containing dimethyl fumarate onto the inert core in a fluidized bed system, such as a fluidized bed spray coating apparatus. A fluidized bed system can also be referred to as a fluid bed.

In certain embodiments, for the pharmaceutical compositions described in the first, second or third embodiment, the weight percentage of dimethyl fumarate is 40%-80%, 50%-75%, 60%-70%, 65%-75%, or 70%-80% of the total weight of the inert core and the first layer. More specifically, the weight percentage of dimethyl fumarate is 68%-72% of the total weight of the inert core and the first layer. In a specific embodiment, the weight percentage of dimethyl fumarate is 70% of the total weight of the inert core and the first layer. Alternatively, the weight percentage of dimethyl fumarate is 60%-63% of the total weight of the inert core and the first layer. In another embodiment, the weight percentage of dimethyl fumarate is 72%-76% of the total weight of the inert core and the first layer. In yet another embodiment, the weight percentage of dimethyl fumarate is 74% of the total weight of the inert core and the first layer.

In certain embodiments, for the pharmaceutical compositions described in the first, second or third embodiment, the first layer further comprises a binder. Exemplary binders include, but are not limited to, acacia, agar, alginic acid, amino methacrylate copolymer, ammonio methacrylate copolymer, ammonio methacrylate copolymer dispersion, calcium carbonate, calcium lactate, carbomer copolymer, carbomer homopolymer, carbomer interpolymer, carboxymethylcellulose sodium, microcrystalline cellulose, silicified microcrystalline cellulose, hydrogenated coconut oil, copovidone, corn syrup, corn syrup solids, dextrates, dextrin, ethyl acrylate and methyl methacrylate copolymer dispersion, ethylcellulose, ethylene glycol and vinyl alcohol graft copolymer, gelatin, liquid glucose, glyceryl behenate, guar gum, hydroxyethyl cellulose, hydroxypropyl cellulose, low-substituted hydroxypropyl cellulose, hypromellose, hypromellose acetate succinate, inulin, alpha-lactalbumin, monohydrate lactose, maltodextrin, maltose, methacrylic acid copolymer, methacrylic acid copolymer dispersion, methacrylic acid and ethyl acrylate copolymer dispersion, methylcellulose, hydrogenated palm oil, polycarbophil, hydrogenated polydextrose, polyethylene oxide, polyvinyl acetate, povidone, pullulan, sodium alginate, pregelatinized starch, pregelatinized modified starch, corn starch, hydroxypropyl corn starch, pregelatinized hydroxypropyl corn starch, pea starch, hydroxypropyl pea starch, pregelatinized hydroxypropyl pea starch, potato starch, hydroxypropyl potato starch, pregelatinized hydroxypropyl potato starch, tapioca starch, wheat starch, hydrogenated starch hydrolysate, sucrose, sunflower oil, syrup, trehalose, hydrogenated vegetable oil, vitamin E polyethylene glycol succinate, zein, hydroxypropyl methylcellulose (HPMC), polyvinylpyrrolidone (PVP), methyl cellulose, ethyl cellulose, sodium carboxy methyl cellulose, polyethylene glycol (PEG), polyvinyl alcohols, polymethacrylate, starch paste, sodium starch, tragacanth, gelatin, alginate, sodium alginate, alginic acid, cellulose, candelilla wax, carnuba wax, copolyvidone, and lactose hydrous. More specifically, the binder is HPMC.

In certain embodiments, for the pharmaceutical compositions described in the first, second or third embodiment, the weight percentage for the binder is 1-25%, 1-20%, or 5-15% of the total weight of the inert core and the first layer. More specifically, the weight percentage for the binder is 5-10% (e.g., 5%, 6%, 7%, 8%, 9% or 10%) of the total weight of the inert core and the first layer. In another specific embodiment, the weight percentage for the binder is 1-5% (e.g., 1%, 2%, 3%, 4% or 5%) total weight of the inert core and the first layer. In a even more specific embodiment, the weight percentage for the binder is 7%.

In certain embodiment, the beads of the present invention have an enteric coating surrounding the first layer comprising dimethyl fumarate. As used herein, "enteric coating" refers to a coating that is stable at the highly acidic pH (e.g., pH~3) found in the stomach, but breaks down rapidly at a less acidic pH (e.g., pH 7-9). Enteric coating materials known in the art can generally be used in the present invention. In one embodiment, for the pharmaceutical compositions described in the first or second embodiment, the enteric coating is layered on the first layer comprising dimethyl fumarate. More specifically, the enteric coating is layered on the first layer by spraying a solution containing enteric coating materials onto the first layer in a fluid bed.

In certain embodiments, for the pharmaceutical compositions described in the third embodiment, the enteric coating is layered on the functional coating. More specifically, the enteric coating is layered on the functional coating by spraying a solution containing the enteric coating materials onto the functional coating in a fluid bed.

In certain embodiments, for the pharmaceutical compositions described in the first, second or third embodiment, the enteric coating comprises an excipient selected from the group consisting of a copolymer of methacrylic acid and methyl methacrylate, a copolymer of methacrylic acid and ethyl acrylate, hypromellose phthalate (HPMCP), cellulose acetate phthalate. More specifically, the enteric coating comprises a copolymer of methacrylic acid and methyl methacrylate. Even more specifically, the ratio of methacrylic acid to methyl methacrylate in the copolymer is 0.8:1 to 1.2:1, (e.g., 1:1). In an even more specific embodiment, the enteric coating comprises EUDRAGIT® L 100 (poly(methacylic acid-co-methyl methacrylate) 1:1).

In certain embodiments, for the pharmaceutical compositions described in the first, second or third embodiment, the enteric coating of the present invention further comprises one or more plasticizers. Exemplary plasticizers include, but are not limited to, acetyltriethyl citrate, benzyl benzoate, castor oil, chlorobutanol, diacetylated monoglycerides, dibutyl sebacate, diethyl phthalate, glycerin, mannitol, polyethylene glycol, polyethylene glycol monomethyl ether, propylene glycol, pullulan, sorbitol, sorbitan sorbitan solution, triacetin, tributyl citrate, triethyl citrate and Vitamin E. In a more specific embodiment, the plasticizer is triethyl citrate.

In one embodiment, for the pharmaceutical compositions described in the first, second or third embodiment, the enteric coating of the present invention comprises EUDRAGIT® L 100 and triethyl citrate. More specifically, the weight ratio of the triethyl citrate to EUDRAGIT® L 100 is from 1:1 to 1:20. Even more specifically, the weight ratio of the triethyl citrate to EUDRAGIT® L 100 is 1:5.

In certain embodiments, for the pharmaceutical compositions described in the first, second or third embodiment, the weight percentage for the enteric coating is 1-20% or 5-15% of the total weight of the inert core and the first layer. More specifically, the weight percentage for the enteric coating is 10-15% (e.g., 10%, 11%, 12%, 13% or 15%) of the total weight of the inert core and the first layer. In another more specific embodiment, the weight percentage for the enteric coating is 11-13% of the total weight of the inert core and the first layer. Even more specifically, the weight percentage of the enteric coating is 12% of the total weight of the inert core and the first layer.

In one embodiment, for the pharmaceutical compositions described in the first, second or third embodiment, the weight percentage for the inert core is 10-60% to the total weight of the inert core and the first layer; the weight percentage for dimethyl fumarate is 40-80% of the total weight of the inert core and the first layer; the weight percentage for the binder is 1-25% of the total weight of the inert core and the first layer; and the weight percentage for the enteric coating is 1-20% of the total weight of the inert core and the first layer. More specifically, the inert core comprises sucrose or starch and the binder is HPMC. Even more specifically, the inert core comprises sucrose or starch; the binder is HPMC and the enteric coating comprises a copolymer of methacrylic acid and methyl methacrylate. In a further more specific embodiment, the inert core comprises sucrose or starch; the binder is HPMC and the enteric coating comprises EUDRAGIT® L 100 (poly(methacylic acid-co-methyl methacrylate) 1:1) and triethyl citrate. Even more specifically, the weight ratio of triethyl citrate to Eudragit L100 is 1:5.

In another embodiment, for the pharmaceutical compositions described in the first, second or third embodiment, the weight percentage for the inert core is 20-40% to the total weight of the inert core and the first layer; the weight percentage for dimethyl fumarate is 50-75% of the total weight of the inert core and the first layer; the weight percentage for the binder is 1-20% of the total weight of the inert core and the first layer; and the weight percentage for the enteric coating is 5-15% of the total weight of the inert core and the first layer. More specifically, the inert core comprises sucrose or starch and the binder is HPMC. Even more specifically, the inert core comprises sucrose or starch; the binder is HPMC and the enteric coating comprises a copolymer of methacrylic acid and methyl methacrylate. In a further more specific embodiment, the inert core comprises sucrose or starch; the binder is HPMC and the enteric coating comprises EUDRAGIT® L 100 (poly(methacylic acid-co-methyl methacrylate) 1:1) and triethyl citrate. Even more specifically, the weight ratio of triethyl citrate to Eudragit L100 is 1:5.

In another embodiment, for the pharmaceutical compositions described in the first, second or third embodiment, the weight percentage for the inert core is 20-30% to the total weight of the inert core and the first layer; the weight percentage for dimethyl fumarate is 65-75% of the total weight of the inert core and the first layer; the weight percentage for the binder is 5-15% of the total weight of the inert core and the first layer; and the weight percentage for the enteric coating is 10-15% of the total weight of the inert core and the first layer. More specifically, the inert core comprises sucrose or starch and the binder is HPMC. Even more specifically, the inert core comprises sucrose or starch; the binder is HPMC and the enteric coating comprises a copolymer of methacrylic acid and methyl methacrylate. In a further more specific embodiment, the inert core comprises sucrose or starch; the binder is HPMC and the enteric coating comprises EUDRAGIT® L 100 (poly(methacylic acid-co-methyl methacrylate) 1:1) and triethyl citrate. Even more specifically, the weight ratio of triethyl citrate to Eudragit L100 is 1:5.

In another embodiment, for the pharmaceutical compositions described in the first, second or third embodiment, the weight percentage for the inert core is 20-24% to the total weight of the inert core and the first layer; the weight percentage for dimethyl fumarate is 68-72% of the total weight of the inert core and the first layer; the weight percentage for the binder is 5-10% of the total weight of the inert core and the first layer; and the weight percentage for the enteric coating is 11-13% of the total weight of the inert core and the first layer. More specifically, the inert core comprises sucrose or starch and the binder is HPMC. Even more specifically, the inert core comprises sucrose or starch; the binder is HPMC and the enteric coating comprises a copolymer of methacrylic acid and methyl methacrylate. In a further more specific embodiment, the inert core comprises sucrose or starch; the binder is HPMC and the enteric coating comprises EUDRAGIT® L 100 (poly(methacylic acid-co-methyl methacrylate) 1:1) and triethyl citrate. Even more specifically, the weight ratio of triethyl citrate to Eudragit L100 is 1:5.

In certain embodiments, for the pharmaceutical compositions described in the second embodiment, the functional coating is layered onto the enteric coating of the beads. More specifically, the functional coating is layered onto the enteric coating by spraying a solution containing functional coating materials onto the enteric coating in a fluid bed.

In certain embodiments, for the pharmaceutical compositions described in the third embodiment, the functional coating is layered onto the first layer of the beads. More specifically, the functional coating is layered onto the first layer by spraying a solution containing functional coating materials onto the functional coating in a fluid bed.

As used herein, the "functional coating" refers to a coating that provides an extended release of the active substance (i.e., dimethyl fumarate). As used herein, "extended release" means that the active substance dimethyl fumarate is released from the pharmaceutical compositions of the present invention in a prolonged manner compared to the immediate-release formulations. The term "prolonged" means that the active substance is released during a longer period of time than the current commercially available formulation of Tecfidera® (dimethyl fumarate), such as at least during a time period that is at least 1.2 times, at least 1.5 times, at least 2 times, at least 3 times, at least 4 times or at least 5 times greater than that of current commercial available formulation of Tecfidera®.

In certain embodiments, for the pharmaceutical compositions described in the second or third embodiment, the functional coating comprises a mixture of one or more water soluble polymers and one or more water insoluble polymers. In certain embodiments, the functional coating comprises one or more excipients selected from the group consisting of polyvinylpyrrolidone (PVP), polyethylene oxide (PEO), glyceryl monostearate, hydroxyl propyl methyl cellulose (HPMC), SoluPlus, polyvinyl alcohol (PVA), polyvinyl alcohol (PVA), hydroxypropylmethylcellulose, acetate succinate (HPMCAS), ethylene vinyl acetate (EVA), methacrylates (Eudragit™), cellulose acetate butyrate (CAB), cellulose acetate phthalate (CAP), poly(ethylene glycol), poly (vinyl acetate) (PVAc), polylactide (PLA), polyglycolide (PGA), copolymers of PLA/PGA and polycaprolactone (PCL), polyvinylpyrrolidone-co-vinyl acetate (Kollidon VA-64), polyrethanes, poly(lactic acid), poly(glycolic acid), poly(anhydride-imides), poly(anhydride-esters), poly(iminocarbonates), poly(phosphazenes), poly(phosphoesters), ethylcellulose (EC), hydroxypropyl cellulose (HPC), alginic acid, carbomer copolymer, carbomer homopolymer, carbomer interpolymer, carboxymethylcellulose sodium, carrageenan, cellaburate, ethylcellulose aqueous dispersion, ethylcellulose dispersion Type B, glyceryl monooleate, guar gum, hydroxypropyl betadex, polyvinyl acetate dispersion, shellac, sodium alginate, pregelatinized starch, pregelatinized modified starch and xanthan gum.

In one embodiment, for the pharmaceutical compositions described in the second or third embodiment, the functional coating of the present invention comprises a mixture of ethylcellulose (EC) and hydroxypropyl cellulose (HPC). More specifically, the functional coating comprises a mixture of ETHOCEL™ 10 (ethylcellulose polymer with viscosity in the range of 9-11 cP for 5% weight solution in 80% toluene and 20% ethanol) and JF Klucel® (hydroxypropyl cellulose polymer with viscosity in the range of 150-400 cP for 5% by weight solution in water). In one embodiment, the weight ratio of ethylcellulose (EC) to hydroxypropyl cellulose (HPC) (e.g., ETHOCEL™ 10 to JF Klucel®) is between 90:10 and 10:90, between 80:20 and 20:80, between 80:20 and 50:50, between 75:25 and 60:40 or between 70:30 and 55:45. More specifically, the weight ratio of ethylcellulose (EC) to hydroxypropyl cellulose (HPC) (e.g., ETHOCEL™ 10 to JF Klucel®) is 70:30. Alternatively, the weight ratio of ethylcellulose (EC) to hydroxypropyl cellulose (HPC) (e.g., ETHOCEL™ 10 to JF Klucel®) is 65:35. In another specific embodiment, the weight ratio of ethylcellulose (EC) to hydroxypropyl cellulose (HPC) (e.g., ETHOCEL™ 10 to JF Klucel®) is 60:40.

In another embodiment, for the pharmaceutical compositions described in the second or third embodiment, the functional coating of the present invention comprises a mixture of Eudragit® RS (poly(ethyl acrylate-co-methyl methacrylate-co-trimethylammonioethyl methacrylate chloride) 1:2:0.1) and Eudragit® RL (poly(ethyl acrylate-co-methyl methacrylate-co-trimetylammonioethyl methacrylate chloride) 1:2:0.2). The weight ratio of Eudragit® RS to Eudragit® RL is between 95:5 and 5:95, between 90:10 and 50:50, between 90:10 and 60:40, or between 85:15 and 70:30. More specifically, the weight ratio of Eudragit® RS to Eudragit® RL is 75:25. Alternatively, the weight ratio of Eudragit® RS to Eudragit® RL is 80:20.

In certain embodiments, for the pharmaceutical compositions described in the second or third embodiment, the weight percentage for the functional coating is 1-30%, 1-20%, 4-12%, 1-10%, 1-7% or 10-15% of the total weight of the inert core and the first layer. More specifically, the weight percentage for the functional coating is 2.0-3.0% of the total weight of the inert core and the first layer. In another more specific embodiment, the weight percentage for the functional coating is 4.0-5.0% of the total weight of the inert core and the first layer. In another more specific embodiment, the weight percentage for the functional coating is 4.5-5.5% of the total weight of the inert core and the first layer. In another more specific embodiment, the weight percentage or the functional coating is 5.0-6.0% of the total weight of the inert core and the first layer. In yet another more specific embodiment, the weight percentage or the functional coating is 11.5-12.5% of the total weight of the inert core and the first layer. Even more specifically, the weight percentage for the functional coating is 2.5% of the total weight of the inert core and the first layer. Alternatively, the weight percentage or the functional coating is 4.5% of the total weight of the inert core and the first layer. In another alternative, the weight percentage or the functional coating is 5.0% of the total weight of the inert core and the first layer. In yet another alternative, the weight percentage or the functional coating is 5.5% of the total weight of the inert core and the first layer. In yet another alternative, the weight percentage or the functional coating is 12% of the total weight of the inert core and the first layer.

In a $1^{st}$ specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 40%-80% of the total weight of the inert core and the first layer and the weight percentage of the binder is 1-25% of the total weight of the inert core and the first layer;

an enteric coating surrounding the first layer, wherein the weight percentage of the enteric coating is 1-20% of the total weight of the inert core and the first layer; and a functional coating surrounding the enteric coating, wherein the weight percentage of the functional coating is 1-30% of the total weight of the inert core and the first layer, wherein the weight percentage of the inert core is 10-60% of the total weight of the inert core and the first layer.

In a 2$^{nd}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 50%-75% of the total weight of the inert core and the first layer and the weight percentage of the binder is 1-20% of the total weight of the inert core and the first layer;

an enteric coating surrounding the first layer, wherein the weight percentage of the enteric coating is 5-15% of the total weight of the inert core and the first layer; and a functional coating surrounding the enteric coating, wherein the weight percentage of the functional coating is 1-20% of the total weight of the inert core and the first layer, wherein the weight percentage of the inert core is 20-40% of the total weight of the inert core and the first layer.

In a 3$^{rd}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 65%-75% of the total weight of the inert core and the first layer and the weight percentage of the binder is 5-15% of the total weight of the inert core and the first layer;

an enteric coating surrounding the first layer, wherein the weight percentage of the enteric coating is 10-15% of the total weight of the inert core and the first layer; and a functional coating surrounding the enteric coating, wherein the weight percentage of the functional coating is 1-10% or 10-15% of the total weight of the inert core and the first layer, wherein the weight percentage of the inert core is 20-30% of the total weight of the inert core and the first layer.

In a 4$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

an enteric coating surrounding the first layer, wherein the weight percentage of the enteric coating is 11-13% of the total weight of the inert core and the first layer; and a functional coating surrounding the enteric coating, wherein the weight percentage of the functional coating is 2.0%-3.0% of the total weight of the inert core and the first layer, wherein the weight percentage of the inert core is 20-24% of the total weight of the inert core and the first layer.

In a 5$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

an enteric coating surrounding the first layer, wherein the weight percentage of the enteric coating is 11-13% of the total weight of the inert core and the first layer; and a functional coating surrounding the enteric coating, wherein the weight percentage of the functional coating is 4.5%-5.5% of the total weight of the inert core and the first layer, wherein the weight percentage of the inert core is 20-24% of the total weight of the inert core and the first layer.

In a 6$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

an enteric coating surrounding the first layer, wherein the weight percentage of the enteric coating is 11-13% of the total weight of the inert core and the first layer; and a functional coating surrounding the enteric coating, wherein the weight percentage of the functional coating is 5.0%-6.0% of the total weight of the inert core and the first layer, wherein the weight percentage of the inert core is 20-24% of the total weight of the inert core and the first layer.

In a 7$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

an enteric coating surrounding the first layer, wherein the weight percentage of the enteric coating is 11-13% of the total weight of the inert core and the first layer; and a functional coating surrounding the enteric coating, wherein the weight percentage of the functional coating is 11.5%-12.5% of the total weight of the inert core and the first layer, wherein the weight percentage of the inert core is 20-24% of the total weight of the inert core and the first layer.

In a 8$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;

an enteric coating surrounding the first layer, wherein the weight percentage of the enteric coating is 11-13% of the total weight of the inert core and the first layer; and a functional coating surrounding the enteric coating, wherein the weight percentage of the functional coating is 2.0%-3.0% of the total weight of the inert core and the first layer, wherein the weight percentage of the inert core is 20-24% of the total weight of the inert core and the first layer.

In a 9th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 4.5%-5.5% of the total weight of the inert core and the first layer,
wherein the weight percentage of the inert core is 20-24% of the total weight of the inert core and the first layer.

In a 10th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 5.0%-6.0% of the total weight of the inert core and the first layer,
wherein the weight percentage of the inert core is 20-24% of the total weight of the inert core and the first layer.

In a 11th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 11.5%-12.5% of the total weight of the inert core and the first layer,
wherein the weight percentage of the inert core is 20-24% of the total weight of the inert core and the first layer.

In a 12th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 4.0%-5.0% of the total weight of the inert core and the first layer,
wherein the weight percentage of the inert core is 20-24% of the total weight of the inert core and the first layer.

In a 13th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 40%-80% of the total weight of the inert core and the first layer and the weight percentage of the binder is 1-25% of the total weight of the inert core and the first layer;
a functional coating surrounding the first layer, wherein the weight percentage of the functional coating is 1-30% of the total weight of the inert core and the first layer; and
an enteric coating surrounding the functional coating, wherein the weight percentage of the enteric coating is 1-20% of the total weight of the inert core and the first layer;
wherein the weight percentage of the inert core is 10-60% of the total weight of the inert core and the first layer.

In a 14th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 50%-75% of the total weight of the inert core and the first layer and the weight percentage of the binder is 1-20% of the total weight of the inert core and the first layer;
a functional coating surrounding the first layer, wherein the weight percentage of the functional coating is 1-20% of the total weight of the inert core and the first layer; and
an enteric coating surrounding the functional coating, wherein the weight percentage of the enteric coating is 5-15% of the total weight of the inert core and the first layer;
wherein the weight percentage of the inert core is 20-40% of the total weight of the inert core and the first layer.

In a 15th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 65%-75% of the total weight of the inert core and the first layer and the weight percentage of the binder is 5-15% of the total weight of the inert core and the first layer;
a functional coating surrounding the first layer, wherein the weight percentage of the functional coating is 1-10%, 4-12%, or 10-15% of the total weight of the inert core and the first layer; and
an enteric coating surrounding the functional coating, wherein the weight percentage of the enteric coating is 10-15% of the total weight of the inert core and the first layer; and
wherein the weight percentage of the inert core is 20-30% of the total weight of the inert core and the first layer.

In a 16th specific embodiment, the pharmaceutical bead composition of the present invention comprises:
an inert core;
a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

a functional coating surrounding the first layer, wherein the weight percentage of the functional coating is 2.0%-3.0% of the total weight of the inert core and the first layer; and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 17$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

a functional coating surrounding the first layer, wherein the weight percentage of the functional coating is 4.5%-5.5% of the total weight of the inert core and the first layer; and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 18$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer; and a functional coating surrounding the first layer, wherein the weight percentage of the functional coating is 5.0%-6.0% of the total weight of the inert core and the first layer, an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 19$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;

a functional coating surrounding the first layer, wherein the weight percentage of the functional coating is 11.5%-12.5% of the total weight of the inert core and the first layer, and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 20$^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;

a functional coating surrounding the first layer, wherein the weight percentage of the functional coating is 2.0%-3.0% of the total weight of the inert core and the first layer; and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 21$^{st}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;

a functional coating surrounding the first layer, wherein the weight percentage of the functional coating is 4.5%-5.5% of the total weight of the inert core and the first layer; and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 22$^{nd}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer; and a functional coating surrounding the first layer, wherein the weight percentage of the functional coating is 5.0%-6.0% of the total weight of the inert core and the first layer, an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a 23$^{rd}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;

a functional coating surrounding the first layer, wherein the weight percentage of the functional coating is 11.5%-12.5% of the total weight of the inert core and the first layer, and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

In a $24^{th}$ specific embodiment, the pharmaceutical bead composition of the present invention comprises:

an inert core;

a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;

a functional coating surrounding the first layer, wherein the weight percentage of the functional coating is 4.5%-5.5% of the total weight of the inert core and the first layer; and an enteric coating surrounding the functional coating, wherein the weight percentage of the enteric coating is 11-13% of the total weight of the inert core and the first layer;

wherein the weight percentage of the inert core is 20-24% of the total weight of the inert core and the first layer.

More specifically, for the pharmaceutical bead composition in the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$ or $24^{th}$ specific embodiment, the inert core comprises sucrose or starch; the binder is HPMC; the enteric coating comprises a copolymer of methacrylic acid and methyl methacrylate and the ratio of methacrylic acid to methyl methacrylate is 1:1; and the functional coating comprises of a mixture of ethylcellulose (EC) and hydroxypropyl cellulose (HPC) and weight ratio of ethylcellulose (EC) to hydroxypropyl cellulose (HPC) is 65:35. More specifically, the enteric coating further comprises triethyl citrate and the weight ratio of the copolymer of methacrylic acid and methyl methacrylate to triethyl citrate is 5:1; and the functional coating comprises a mixture of ETHOCEL™ 10 (ethylcellulose polymer with viscosity in the range of 9-11 cP for 5% weight solution in 80% toluene and 20% ethanol) and JF Klucel® (hydroxypropyl cellulose polymer with viscosity in the range of 150-400 cP for 5% by weight solution in water), wherein the weight ratio of ETHOCEL™ 10 to JF Klucel® is 65:35.

In another more specific embodiment, for the pharmaceutical bead composition in the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$ or $24^{th}$ specific embodiment, the inert core comprises sucrose or starch; the binder is HPMC; the enteric coating comprises a copolymer of methacrylic acid and methyl methacrylate and the ratio of methacrylic acid to methyl methacrylate is 1:1; and the functional coating comprises of a mixture of ethylcellulose (EC) and hydroxypropyl cellulose (HPC) and weight ratio of ethylcellulose (EC) to hydroxypropyl cellulose (HPC) is 60:40. More specifically, the enteric coating further comprises triethyl citrate and the weight ratio of the copolymer of methacrylic acid and methyl methacrylate to triethyl citrate is 5:1; and the functional coating comprises a mixture of ETHOCEL™ 10 (ethylcellulose polymer with viscosity in the range of 9-11 cP for 5% weight solution in 80% toluene and 20% ethanol) and JF Klucel® (hydroxypropyl cellulose polymer with viscosity in the range of 150-400 cP for 5% by weight solution in water), wherein the weight ratio of ETHOCEL™ 10 to JF Klucel® is 60:40.

In a fourth embodiment, the present invention is directed to a pharmaceutical composition in the form of a bead comprising:

a core comprising dimethyl fumarate; and an enteric coating surrounding the core.

In a fifth embodiment, the pharmaceutical composition described in the fourth embodiment can further comprise a functional coating surrounding the enteric coating.

In a sixth embodiment, the present invention is directed to a pharmaceutical composition in the form of a bead comprising:

a core comprising dimethyl fumarate;

a functional coating surrounding the core; and an enteric coating surrounding the functional core.

In certain embodiments, for the pharmaceutical compositions of the fourth, fifth or sixth embodiment, the DMF core is a sphere having a diameter of 0.5-2.0 mm. More specifically, the sphere has a diameter of 0.5-1.5 mm. In another specific embodiment, the sphere has a diameter of 0.6-2.0 mm.

In certain embodiments, for the pharmaceutical compositions of the fourth, fifth or sixth embodiment, the weight percentage of dimethyl fumarate is 40%-80% of the total weight of the core. The weight of the core is the total weight of each ingredient in the core, excluding exterior coating, such as an enteric coating. More specifically, the weight percentage of dimethyl fumarate is 60%-80%, 60-70% or 70-80% of the total weight of the core. Even more specifically, the weight percentage of dimethyl fumarate is 65% of the total weight of the core. Alternatively, the weight percentage of dimethyl fumarate is 75% of the total weight of the core.

In certain embodiments, for the pharmaceutical compositions of the fourth, fifth or sixth embodiment, the core further comprises a binder. Exemplary binders include, but are not limited to, acacia, agar, alginic acid, amino methacrylate copolymer, ammonio methacrylate copolymer, ammonio methacrylate copolymer dispersion, calcium carbonate, calcium lactate, carbomer copolymer, carbomer homopolymer, carbomer interpolymer, carboxymethylcellulose sodium, microcrystalline cellulose, silicified microcrystalline cellulose, hydrogenated coconut oil, copovidone, corn syrup, corn syrup solids, dextrates, dextrin, ethyl acrylate and methyl methacrylate copolymer dispersion, ethylcellulose, ethylene glycol and vinyl alcohol graft copolymer, gelatin, liquid glucose, glyceryl behenate, guar gum, hydroxyethyl cellulose, hydroxypropyl cellulose, low-substituted hydroxypropyl cellulose, hypromellose, hypromellose acetate succinate, inulin, alpha-lactalbumin, monohydrate lactose, maltodextrin, maltose, methacrylic acid copolymer, methacrylic acid copolymer dispersion, methacrylic acid and ethyl acrylate copolymer dispersion, methylcellulose, hydrogenated palm oil, polycarbophil, hydrogenated polydextrose, polyethylene oxide, polyvinyl acetate, povidone, pullulan, sodium alginate, pregelatinized starch, pregelatinized modified starch, corn starch, hydroxypropyl corn starch, pregelatinized hydroxypropyl corn starch, pea starch, hydroxypropyl pea starch, pregelatinized hydroxypropyl pea starch, potato starch, hydroxypropyl potato starch, pregelatinized hydroxypropyl potato starch, tapioca starch, wheat starch, hydrogenated starch hydrolysate, sucrose, sunflower oil, syrup, trehalose, hydrogenated vegetable oil, vitamin E polyethylene glycol succinate, zein, hydroxypropyl methylcellulose (HPMC), polyvinylpyrrolidone (PVP), methyl cellulose, ethyl cellulose, sodium carboxy methyl cellulose, polyethylene glycol (PEG), polyvinyl alcohols, polymethacrylate, starch paste, sodium starch, tragacanth, gelatin, alginate, sodium alginate, alginic acid, cellulose, candelilla wax, carnuba wax, copolyvidone, and lactose hydrous. In one embodiment, the binder is microcrystalline cellulose or starch.

The binder can be present in an amount of 1-50% by weight of the core. More specifically, the binder can be present in an amount of 15-35%.

In certain embodiments, for the pharmaceutical compositions of the fourth or fifth embodiment, the enteric coating is layered on the dimethyl fumarate core. More specifically, the enteric coating is layered on the core by spraying a solution containing enteric coating materials onto the dimethyl fumarate core in a fluid bed.

In certain embodiments, for the pharmaceutical composition of the sixth embodiment, the enteric coating is layered on the functional coating. More specifically, the enteric coating is layered on the functional coating by spraying a solution containing the enteric coating materials onto the functional coating in a fluid bed.

In certain embodiments, for the pharmaceutical compositions of the fourth, fifth or sixth embodiment, the enteric coating comprises an excipient selected from the group consisting of a copolymer of methacrylic acid and methyl methacrylate, a copolymer of methacrylic acid and ethyl acrylate, hypromellose phthalate (HPMCP), cellulose acetate phthalate. More specifically, the enteric coating comprises a copolymer of methacrylic acid and methyl methacrylate. Even more specifically, the ratio of methacrylic acid to methyl methacrylate in the copolymer is 0.8:1 to 1.2:1, (e.g., 1:1). In an even more specific embodiment, the enteric coating comprises EUDRAGIT® L 100 (poly (methacylic acid-co-methyl methacrylate) 1:1).

In certain embodiments, for the pharmaceutical compositions of the fourth, fifth or sixth embodiment, the enteric coating of the present invention further comprises one or more plasticizers. Exemplary plasticizers include, but are not limited to, acetyltriethyl citrate, benzyl benzoate, castor oil, chlorobutanol, diacetylated monoglycerides, dibutyl sebacate, diethyl phthalate, glycerin, mannitol, polyethylene glycol, polyethylene glycol monomethyl ether, propylene glycol, pullulan, sorbitol, sorbitol sorbitan solution, triacetin, tributyl citrate, triethyl citrate and Vitamin E. In a more specific embodiment, the plasticizer is triethyl citrate.

In one embodiment, for the pharmaceutical compositions of the fourth, fifth or sixth embodiment, the enteric coating of the present invention comprises EUDRAGIT® L 100 and triethyl citrate. More specifically, the weight ratio of the triethyl citrate to EUDRAGIT® L 100 is from 1:1 to 1:20. Even more specifically, the weight ratio of the triethyl citrate to EUDRAGIT® L 100 is 1:5.

In certain embodiments, for the pharmaceutical compositions of the fourth, fifth or sixth embodiment, the weight percentage for the enteric coating is 1-20% or 5-15% of the total weight of the core. More specifically, the weight percentage for the enteric coating is 10-15% (e.g., 10%, 11%, 12%, 13% or 15%) of the total weight of the core. In another more specific embodiment, the weight percentage for the enteric coating is 11-13% of the total weight of the core. Even more specifically, the weight percentage of the enteric coating is 12% of the total weight of the core.

In certain embodiments, for the pharmaceutical compositions of the fifth or sixth embodiment, the functional coating comprises a mixture of one or more water soluble polymers and one or more water insoluble polymers. In certain embodiments, the functional coating comprises one or more excipients selected from the group consisting of polyvinylpyrrolidone (PVP), polyethylene oxide (PEO), glyceryl monostearate, hydroxyl propyl methyl cellulose (HPMC), SoluPlus, polyvinyl alcohol (PVA), polyvinyl alcohol (PVA), hydroxypropylmethylcellulose, acetate succinate (HPMCAS), ethylene vinyl acetate (EVA), methacrylates (Eudragit™), cellulose acetate butyrate (CAB), cellulose acetate phthalate (CAP), poly(ethylene glycol), poly (vinyl acetate) (PVAc), polylactide (PLA), polyglycolide (PGA), copolymers of PLA/PGA and polycaprolactone (PCL), polyvinylpyrrolidone-co-vinyl acetate (Kollidon VA-64), polyrethanes, poly(lactic acid), poly(glycolic acid), poly(anhydride-imides), poly(anhydride-esters), poly(iminocarbonates), poly(phosphazenes), poly(phosphoesters), ethylcellulose (EC), hydroxypropyl cellulose (HPC), alginic acid, carbomer copolymer, carbomer homopolymer, carbomer interpolymer, carboxymethylcellulose sodium, carrageenan, cellaburate, ethylcellulose aqueous dispersion, ethylcellulose dispersion Type B, glyceryl monooleate, guar gum, hydroxypropyl betadex, polyvinyl acetate dispersion, shellac, sodium alginate, pregelatinized starch, pregelatinized modified starch and xanthan gum.

In one embodiment, for the pharmaceutical compositions of the fifth or sixth embodiment, the functional coating comprises a mixture of ethylcellulose (EC) and hydroxypropyl cellulose (HPC). More specifically, the functional coating comprises a mixture of ETHOCEL™ 10 (ethylcellulose polymer with viscosity in the range of 9-11 cP for 5% weight solution in 80% toluene and 20% ethanol) and JF Klucel® (hydroxypropyl cellulose polymer with viscosity in the range of 150-400 cP for 5% by weight solution in water). In one embodiment, the weight ratio of ethylcellulose (EC) to hydroxypropyl cellulose (HPC) (e.g., ETHOCEL™ 10 to JF Klucel®) is between 90:10 and 10:90, between 80:20 and 20:80, between 80:20 and 50:50, between 75:25 and 60:40, or between 70:30 and 55:45. More specifically, the weight ratio of ethylcellulose (EC) to hydroxypropyl cellulose (HPC) (e.g., ETHOCEL™ 10 to JF Klucel®) is 70:30. Alternatively, the weight ratio of ethylcellulose (EC) to hydroxypropyl cellulose (HPC) (e.g., ETHOCEL™ 10 to JF Klucel®) is 65:35. In another alternative, the weight ratio of ethylcellulose (EC) to hydroxypropyl cellulose (HPC) (e.g., ETHOCEL™ 10 to JF Klucel®) is 60:40.

In another embodiment, for the pharmaceutical compositions of the fifth or sixth embodiment, the functional coating comprises a mixture of Eudragit® RS (poly(ethyl acrylate-co-methyl methacrylate-co-trimethylammonioethyl methacrylate chloride) 1:2:0.1) and Eudragit® RL (poly(ethyl acrylate-co-methyl methacrylate-co-trimetylammonioethyl methacrylate chloride) 1:2:0.2). The weight ratio of Eudragit® RS to Eudragit® RL is between 95:5 and 5:95, between 90:10 and 50:50, between 90:10 and 60:40, or between 85:15 and 70:30. More specifically, the weight ratio of Eudragit® RS to Eudragit® RL is 75:25. Alternatively, the weight ratio of Eudragit® RS to Eudragit® RL is 80:20.

In certain embodiments, for the pharmaceutical compositions of the fifth or sixth embodiment, the weight percentage for the functional coating is 1-30%, 1-20%, 4-12%, 1-10%, 1-7% or 10-15% of the total weight of the inert core and the first layer. More specifically, the weight percentage for the functional coating is 2.0-3.0% of the total weight of the inert core and the first layer. In another more specific embodiment, the weight percentage for the functional coating is 4.5-5.5% of the total weight of the inert core and the first layer. In another more specific embodiment, the weight percentage for the functional coating is 4.0-5.0% of the total weight of the inert core and the first layer. In another more specific embodiment, the weight percentage or the functional coating is 5.0-6.0% of the total weight of the inert core and the first layer. In yet another more specific embodiment, the weight percentage or the functional coating is 11.5-12.5% of the total weight of the inert core and the first layer. Even more specifically, the weight percentage for the functional coating is 2.5% of the total weight of the inert core and the first layer. Alternatively, the weight percentage or the functional coating is 4.5% of the total weight of the inert core and the first layer. In another alternative, the weight percentage or the functional coating is 5.0% of the total weight of the inert core and the first layer. In yet another alternative, the weight percentage or the functional coating is 5.5% of the total weight of the inert core and the first layer. In yet another alternative, the weight percentage or the functional coating is 12% of the total weight of the inert core and the first layer.

In a $25^{th}$ specific embodiment, the pharmaceutical bead composition of the present invention comprises:
a core comprising dimethyl fumarate;
an enteric coating surrounding the core, wherein the weight percentage of the enteric coating is 11%-13% of the total weight of the core; and
a functional coating surrounding the enteric coating, wherein the weight percentage of the functional coating is 2.0%-3.0% of the total weight of the core,
wherein the weight percentage of dimethyl fumarate is 60%-80% of the total weight the core.

In a $26^{th}$ specific embodiment, the pharmaceutical bead composition of the present invention comprises:
a core comprising dimethyl fumarate;
an enteric coating surrounding the core, wherein the weight percentage of the enteric coating is 11%-13% of the total weight of the core; and
a functional coating surrounding the enteric coating, wherein the weight percentage of the functional coating is 4.5%-5.5% of the total weight of the core,
wherein the weight percentage of dimethyl fumarate is 60%-80% of the total weight the core.

In a $27^{th}$ specific embodiment, the pharmaceutical bead composition of the present invention comprises:
a core comprising dimethyl fumarate;
an enteric coating surrounding the core, wherein the weight percentage of the enteric coating is 11%-13% of the total weight of the core; and
a functional coating surrounding the enteric coating, wherein the weight percentage of the functional coating is 5.0%-6.0% of the total weight of the core,
wherein the weight percentage of dimethyl fumarate is 60%-80% of the total weight the core.

In a $28^{th}$ specific embodiment, the pharmaceutical bead composition of the present invention comprises:
a core comprising dimethyl fumarate;
an enteric coating surrounding the core, wherein the weight percentage of the enteric coating is 11%-13% of the total weight of the core; and
a functional coating surrounding the enteric coating, wherein the weight percentage of the functional coating is 11.5%-12.50% of the total weight of the core,
wherein the weight percentage of dimethyl fumarate is 60%-80% of the total weight the core.

In a $29^{th}$ specific embodiment, the pharmaceutical bead composition of the present invention comprises:
a core comprising dimethyl fumarate;
an enteric coating surrounding the core, wherein the weight percentage of the enteric coating is 11%-13% of the total weight of the core; and
a functional coating surrounding the enteric coating, wherein the weight percentage of the functional coating is 4.0%-5.0% of the total weight of the core,
wherein the weight percentage of dimethyl fumarate is 60%-80% of the total weight the core.

In a $30^{th}$ specific embodiment, the pharmaceutical bead composition of the present invention comprises:
a core comprising dimethyl fumarate;
a functional coating surrounding the core, wherein the weight percentage of the functional coating is 2.0%-3.0% of the total weight of the core;
an enteric coating surrounding the functional coating, wherein the weight percentage of the enteric coating is 11%-13% of the total weight of the core;
wherein the weight percentage of dimethyl fumarate is 60%-80% of the total weight the core.

In a $31^{st}$ specific embodiment, the pharmaceutical bead composition of the present invention comprises:
a core comprising dimethyl fumarate;
a functional coating surrounding the core, wherein the weight percentage of the functional coating is 4.5%-5.5% of the total weight of the core; and
an enteric coating surrounding the functional coating, wherein the weight percentage of the enteric coating is 11%-13% of the total weight of the core;
wherein the weight percentage of dimethyl fumarate is 60%-80% of the total weight the core.

In a $32^{nd}$ specific embodiment, the pharmaceutical bead composition of the present invention comprises:
a core comprising dimethyl fumarate;
a functional coating surrounding the core, wherein the weight percentage of the functional coating is 5.0%-6.0% of the total weight of the core; and
an enteric coating surrounding the functional coating, wherein the weight percentage of the enteric coating is 11%-13% of the total weight of the core;
wherein the weight percentage of dimethyl fumarate is 60%-80% of the total weight the core.

In a $33^{rd}$ specific embodiment, the pharmaceutical bead composition of the present invention comprises:
a core comprising dimethyl fumarate;
a functional coating surrounding the core, wherein the weight percentage of the functional coating is 11.5%-12.5% of the total weight of the core; and
an enteric coating surrounding the functional coating, wherein the weight percentage of the enteric coating is 11%-13% of the total weight of the core;
wherein the weight percentage of dimethyl fumarate is 60%-80% of the total weight the core.

In a $34^{th}$ specific embodiment, the pharmaceutical bead composition of the present invention comprises:
a core comprising dimethyl fumarate;
a functional coating surrounding the core, wherein the weight percentage of the functional coating is 4.0%-5.0%% of the total weight of the core; and
an enteric coating surrounding the functional coating, wherein the weight percentage of the enteric coating is 11%-13% of the total weight of the core;
wherein the weight percentage of dimethyl fumarate is 60%-80% of the total weight the core.

More specifically, for the pharmaceutical compositions in the $25^{th}$, $26^{th}$, $27^{th}$, $28^{th}$, $29^{th}$, $30^{th}$, $31^{st}$, $32^{nd}$, $33^{rd}$ or $34^{th}$ specific embodiment, the enteric coating comprises a copolymer of methacrylic acid and methyl methacrylate and the ratio of methacrylic acid to methyl methacrylate is 1:1; and the functional coating comprises of a mixture of ethylcellulose (EC) and hydroxypropyl cellulose (HPC) and weight ratio of ethylcellulose (EC) to hydroxypropyl cellulose (HPC) is 65:35. More specifically, the enteric coating further comprises triethyl citrate and the weight ratio of the copolymer of methacrylic acid and methyl methacrylate to triethyl citrate is 5:1; and the functional coating comprises a mixture of ETHOCEL™ 10 (ethylcellulose polymer with viscosity in the range of 9-11 cP for 5% weight solution in 80% toluene and 20% ethanol) and JF Klucel® (hydroxypropyl cellulose polymer with viscosity in the range of 150-400 cP for 5% by weight solution in water), wherein the weight ratio of ETHOCEL™ 10 to JF Klucel® is 65:35.

In another more specific embodiment, for the pharmaceutical compositions in the $25^{th}$, $26^{th}$, $27^{th}$, $28^{th}$, $29^{th}$, $30^{th}$, $31^{st}$, $32^{nd}$, $33^{rd}$ or $34^{th}$ specific embodiment, the enteric coating comprises a copolymer of methacrylic acid and methyl methacrylate and the ratio of methacrylic acid to methyl methacrylate is 1:1; and the functional coating comprises of a mixture of ethylcellulose (EC) and hydroxypropyl cellulose (HPC) and weight ratio of ethylcellulose (EC) to hydroxypropyl cellulose (HPC) is 60:40. More specifically, the enteric coating further comprises triethyl citrate and the weight ratio of the copolymer of methacrylic acid and methyl methacrylate to triethyl citrate is 5:1; and the functional coating comprises a mixture of ETHOCEL™ 10 (ethylcellulose polymer with viscosity in the range of 9-11 cP for 5% weight solution in 80% toluene and 20% ethanol) and JF Klucel® (hydroxypropyl cellulose polymer with viscosity in the range of 150-400 cP for 5% by weight solution in water), wherein the weight ratio of ETHOCEL™ 10 to JF Klucel® is 60:40.

In certain embodiments, the pharmaceutical compositions described in the second embodiment, the fifth embodiment or in the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $25^{th}$, $26^{th}$, $27^{th}$, $28^{th}$ or $29^{th}$ specific embodiment can further comprise a second enteric coating surrounding the functional coating. Any enteric coating described above can be used as the second enteric coating.

In certain embodiment, the second enteric coating is layered on the functional coating. More specifically, the second enteric coating is layered on the functional coating by spraying a solution containing the enteric coating materials onto the functional coating in a fluid bed.

In certain embodiment, the second enteric coating comprises an excipient selected from the group consisting of a copolymer of methacrylic acid and methyl methacrylate, a copolymer of methacrylic acid and ethyl acrylate, hypromellose phthalate (HPMCP), cellulose acetate phthalate. More specifically, the second enteric coating comprises a copolymer of methacrylic acid and methyl methacrylate. Even more specifically, the ratio of methacrylic acid to methyl methacrylate in the copolymer is 0.8:1 to 1.2:1, (e.g., 1:1). In an even more specific embodiment, the enteric coating comprises EUDRAGIT® L 100 (poly(methacylic acid-co-methyl methacrylate) 1:1).

In certain embodiments, the second enteric coating further comprises one or more plasticizers. Exemplary plasticizers include, but are not limited to, acetyltriethyl citrate, benzyl benzoate, castor oil, chlorobutanol, diacetylated monoglycerides, dibutyl sebacate, diethyl phthalate, glycerin, mannitol, polyethylene glycol, polyethylene glycol monomethyl ether, propylene glycol, pullulan, sorbitol, sorbitol sorbitan solution, triacetin, tributyl citrate, triethyl citrate and Vitamin E. In a more specific embodiment, the plasticizer is triethyl citrate.

In one embodiment, the second enteric coating of the present invention comprises EUDRAGIT® L 100 and triethyl citrate. More specifically, the weight ratio of the triethyl citrate to EUDRAGIT® L 100 is from 1:1 to 1:20. Even more specifically, the weight ratio of the triethyl citrate to EUDRAGIT® L 100 is 1:5.

In certain embodiments, the weight percentage for the second enteric coating is 1-20% or 5-15% of the total weight of the inert core and the first layer. More specifically, the weight percentage for the enteric coating is 10-15% (e.g., 10%, 11%, 12%, 13% or 15%) of the total weight of the inert core and the first layer. In another more specific embodiment, the weight percentage for the enteric coating is 11-13% of the total weight of the inert core and the first layer. Even more specifically, the weight percentage of the enteric coating is 12% of the total weight of the inert core and the first layer.

The pharmaceutical bead compositions of the present invention provide extended release of the active substance dimethyl fumarate when subjected to a dissolution test. The dissolution test can be carried out according to standard procedures published by USP-NF.

In one embodiment, the dissolution profile of the tablets of the present invention is determined by subjecting the tablets to an in vitro dissolution test employing 0.1 N hydrochloric acid as dissolution medium during the first 2 hours of the test and then USP Simulated Intestinal Fluid (SIF) without pancreatin as dissolution medium in a USP Apparatus II (paddle apparatus) (Test 1). Alternatively, the dissolution profile is determined by subjecting the tablets of the present invention to an in vitro dissolution test employing USP Simulated Gastric Fluid (SGF) without pepsin as dissolution medium during the first 2 hours of the test and then USP Simularted Intestinal Fluid (SIF) without pancreatin as dissolution medium in a USP Apparatus IV (flow-through cell) (Test 2). In yet another alternative, the dissolution profile is determined by subjecting the tablets of the present invention to an in vitro dissolution test employing USP Simularted Intestinal Fluid (SIF) without pancreatin in a USP Apparatus IV (flow-through cell) (Test 3). USP SIF ans SGF solutions can be prepared according to according to procedures described in USP35-NF30.

In certain embodiments, when subjected to dissolution Test 1, the pharmaceutical bead composition of the present invention has the following dissolution profile:

within the first 2 hours of the test, less than 10% by weight of the active substance in the tablet is released;

within the first 4 hours of the test, 10-70% by weight of the active substance in the tablet is released; and within the first 7 hours of the test, 50-100% by weight of the active substance in the tablet is released.

In certain embodiments, when subjected to dissolution Test 1, the tablet composition of the present invention has the following dissolution profile:

within the first 2 hours of the test, less than 10% by weight of the active substance in the tablet is released; and within the first 4 hours of the test, 90-100% by weight of the active substance in the tablet is released.

In certain embodiments, when subjected to dissolution Test 2, the bead composition of the present invention has the following dissolution profile:

within the first 2 hours of the test, less than 10% by weight of the active substance in the tablet is released;

within the first 4 hours of the test, 10-70% by weight of the active substance in the tablet is released; and within the first 9 hours of the test, 50-100% by weight of the active substance in the table is released.

In certain embodiments, when subjected to dissolution Test 2, the bead composition of the present invention has the following dissolution profile:

within the first 2 hours of the test, less than 10% by weight of the active substance in the tablet is released;

within the first 4 hours of the test, 70-90% by weight of the active substance in the tablet is released; and within the first 9 hours of the test, 90-100% by weight of the active substance in the table is released.

In certain embodiments, the pharmaceutical composition of the present invention releases 80% of dimethyl fumarate from the composition within 3-10 hours, preferably within 4-8 hours, more preferably within 4-6 hours in an in vivo pharmacokinetic study described herein. In particular, dogs were administered with the pharmaceutical composition of the present invention containing 240 mg of DMF.

In certain embodiments, the amount of dimethyl fumarate in the pharmaceutical compositions described herein is from is from 90 mg to 960 mg, more specifically from 120 mg to 480 mg. In one embodiment, the amount of dimethyl fumarate in a single capsule described herein is 240 mg. Alternatively, the amount of dimethyl fumarate in a single capsule described herein is 480 mg.

The present invention also provides a method of treating a subject having multiple sclerosis (e.g., relapsing-remitting MS, secondary progressive MS, primary progressive MS, progressive relapsing MS) comprising administering to the subject an effective amount of a pharmaceutical composition described herein. In one embodiment, the method of the present invention is for treating relapsing-remitting MS.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

As used herein, the term "subject" and the term "patient" can be used interchangeable and they refer to a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The effective amount or therapeutic dosage of the pharmaceutical compositions described herein that is administered to treat a patient depends on a number of factors, which include, but are not limited to, weight and age of the patient, route of administration, the underlying causes of the disease to be treated, and the severity of the disease to be treated. In one embodiment, the effective dosage can range from 1 mg/kg to 50 mg/kg (e.g., from 2.5 mg/kg to 20 mg/kg or from 2.5 mg/kg to 15 mg/kg). In one embodiment, an effective amount of DMF to be administered to a subject, for example orally, can be from 0.1 g to 1 g per day, for example, from 200 mg to 800 mg per day (e.g., from 240 mg to 720 mg per day; or from 480 mg to 720 mg per day; or 480 mg per day; or 720 mg per day).

The daily dose can range, but is not limited to, a total amount of 60 mg to 800 mg, 60 mg to 720 mg, 60 mg to 500 mg, 60 mg to 480 mg, 60 mg to 420 mg, 60 mg to 360 mg, 60 mg to 240 mg, 60 mg to 220 mg, 60 mg to 200 mg, 60 mg to 180 mg, 60 mg to 160 mg, 60 mg to 140 mg, 60 mg to 120 mg, 60 mg to 100 mg, 60 mg to 80 mg, 80 mg to 480 mg, 100 mg to 480 mg, 120 mg to 480 mg, 140 mg to 480 mg, 160 mg to 480 mg, 180 mg to 480 mg, 200 mg to 480 mg, 220 mg to 480 mg, 240 mg to 480 mg, 300 mg to 480 mg, 360 mg to 480 mg, 400 mg to 480 mg, 450 mg to 500 mg, 480 mg to 500 mg, 80 to 400 mg, 100 to 300 mg, 120 to 180 mg, or 140 mg to 160 mg.

In one embodiment, the daily dosage is 240 mg. Alternatively, the daily dosage is 480 mg.

The daily dose(s) of DMF may be administered in a single administration or in separate administrations of 2, 3, 4, or 6 equal doses. In one embodiment, the effective daily dose is 480 mg per day and is administered in one dose to a subject in need thereof. In another embodiment, the effective daily dose is 240 mg per day and is administered in one dose to a subject in need thereof.

In one embodiment, the pharmaceutical composition of the present invention is administered at least one hour before or after food is consumed by the subject in need thereof. In case the subject experiences side effects (e.g., flushing or GI discomfort), the subject can consume food shortly (e.g., 30 mins to an hour) before administered the pharmaceutical composition.

In one embodiment, the subject administered the pharmaceutical compositions of the present invention may take one or more non-steroidal anti-inflammatory drugs (e.g., aspirin) before (for example, 10 minutes to an hour, e.g., 30 minutes before) taking the pharmaceutical composition. In one embodiment, the subject administered the pharmaceutical composition takes the one or more non-steroidal anti-inflammatory drugs (e.g., aspirin) to control side effects (e.g., flushing). In another embodiment, the one or more non-steroidal anti-inflammatory drugs is selected from a group consisting of aspirin, ibuprofen, naproxen, ketoprofen, celecoxib, MK-0524, and combinations thereof. The one or more non-steroidal anti-inflammatory drugs can be administered in an amount of 50 mg to 500 mg before taking the dosage form described above. In one embodiment, a subject takes 325 mg aspirin before taking each dosage form described above.

In one embodiment, the subject in need of the treatment is administered a first dose of the pharmaceutical compositions described herein for a first dosing period; and administered a second dose of the pharmaceutical compositions described herein for a second dosing period. In one embodiment, the first dose is lower than the second dose (e.g., the first dose is half of the second dose). In one embodiment, the first dosing period is at least one week (e.g., 1-4 weeks). In one embodiment, the first dose of the pharmaceutical compositions comprises 240 mg of DMF and the pharmaceutical composition is administered to the subject once daily for the first dosing period. In one embodiment, the second dose of the pharmaceutical composition comprises 480 mg of DMF and the pharmaceutical composition is administered to the subject once daily for the second dosing period. In one embodiment, if the subject, after being administered the dose at the second dosing period, experiences more than expected level of side effects (e.g., flushing or a gastrointestinal disturbance), the subject can use a lower dose (e.g., the dose at the first dosing period) for a period (e.g., 1-4 weeks or more) sufficient to allow the side effects to decrease before returning to the dose at the second dosing period.

In one embodiment, the first dose of the pharmaceutical composition comprises 240 mg of DMF and the pharmaceutical composition is administered to the subject once daily for at least one week, and the second dose of the pharmaceutical composition comprises 480 mg of DMF and the pharmaceutical composition is administered to the subject once daily for at least two weeks.

In one embodiment, the subject is administered a first dose for one week and a second dose for a second dosing period of at least 48 weeks. In another embodiment, the subject is administered a first dose for one week and a second dose for a second dosing period of at least two years. In another embodiment, the subject is administered a first dose for one week and a second dose until the subject does not require treatment.

In certain embodiments, the methods of treating a subject having multiple sclerosis described herein further comprises administering to the subject a second therapeutic agent.

In one embodiment, the second therapeutic agents is a disease modifying agent. In one embodiment, the second therapeutic agents alleviate the side effects of dimethyl fumarate. For example, the second therapeutic agent can be a therapeutic agent that can reduce the flushing (e.g., aspirin) or GI disturbance (e.g., loperamide).

In another embodiment, the second therapeutic agent is a Nrf-2 modulator.

In yet another embodiment, the second therapeutic agents can be, e.g., interferon beta-la (Avonex®, Rebif®), glatiramer (Copaxone®), modafinil, azathioprine, predisolone, mycophenolate, mofetil, mitoxantrone, natalizumab (Tysabri®), sphinogosie-1 phosphate modulator e.g., fingolimod (Gilenya®), and other drugs useful for MS treatment such as teriflunornide (Aubagio®), piroxicam, and phenidone.

The pharmaceutical DMF compositions of the present invention and the second therapeutic agent may be administered concurrently (as separate compositions or together in a single dosage form) or consecutively over overlapping or non-overlapping intervals. In the sequential administration, the DMF composition and the second therapeutic agent can be administered in any order. In some embodiments, the length of an overlapping interval is more than 2, 4, 6, 12, 24, 48 weeks or longer.

In order that the invention described herein may be more fully understood, the following examples are set forth. It should be understood that these examples are for illustrative purposes only and are not to be construed as limiting this invention in any manner.

EXAMPLES

Example 1. Methods for Preparing Pharmaceutical Compositions of the Present Invention The following coating processes are conducted using a fluid bed granulator with a Wurster insert. API dimethyl fumarate was first layered onto the surface of sugar spheres by spraying a DMF containing solution (Table 1) onto the sugar spheres in a fluid bed.

TABLE 1

DMF solution formulation

| Ingredients | Weight % |
|---|---|
| DMF | 21% |
| HPMC (HPMC E5) | 2% |
| Ethanol (96% v/v) | 62% |
| DI Water | 15% |
| TOTAL | 100% |

The API layered spheres were then enteric coated for acid protection.

TABLE 2

Enteric coat formulation

| Ingredients | Weight % |
|---|---|
| Eudragit L100 (Methacylic acid-methyl methacrylate copolymer) | 6.5% |
| IPA | 90.7% |
| Water | 1.5% |
| Triethyl citrate | 1.3% |
| TOTAL | 100% |

A sustained release functional coating (Tables 3, 4, 5 and 6) was then applied to the enteric coated spheres.

TABLE 3

Coating solution formulation for EC/HPC 65/35

| Ingredients | Weight % |
|---|---|
| EC (Ethocel 10) | 3.9 |
| HPC (Klucel JF) | 2.1 |
| Water | 11.3 |
| IPA | 82.7 |
| TOTAL | 100% |

TABLE 4

Coating solution formulation for EC/HPC 70/30

| Ingredients | Weight % |
|---|---|
| EC (Ethocel 10) | 4.2 |
| HPC (Klucel JF) | 1.8 |
| Water | 11.3 |
| IPA | 82.7 |
| TOTAL | 100% |

TABLE 5

Coating solution formulation for RS/RL 75/25

| Ingredients | Weight % |
|---|---|
| Eudragit RS | 4.5 |
| Eudragit RL | 1.5 |
| Water | 11.3 |
| IPA | 82.7 |
| TOTAL | 100% |

TABLE 6

Coating solution formulation for RS/RL 80/20

| Ingredients | Weight % |
|---|---|
| Eudragit RS | 4.8 |
| Eudragit RL | 1.2 |
| Water | 11.3 |
| IPA | 82.7 |
| TOTAL | 100% |

Specifically, Formulation D is prepared according to the general procedure described above using DMF solution described in Table 1 and enteric coating solution described in Table 2. Formulation D has no functional coating. Formulations E and F are prepared according to the procedures for Formulation D and is further coated with functional coating solution described in Table 3. The weight percentages of the functional coating in Formulation E is 2.5% of the total weight of the sugar sphere and DMF layer. The weight percentages of the functional coating in Formulation F is 5.0% of the total weight of the sugar sphere and DMF layer. Formulations D, E and F are beads having a diameter of 1-1.2 mm.

Formulation A is prepared according to the general procedure described above using DMF solution described in Table 1, enteric coating solution described in Table 2 and functional coating solution described in Table 3a below.

TABLE 3a

Coating solution formulation for EC/HPC 60/40

| Ingredients | Weight % |
|---|---|
| EC (Ethocel 10) | 3.6 |
| HPC (Klucel JF) | 2.4 |
| Water | 11.3 |
| IPA | 82.7 |
| TOTAL | 100% |

The weight percentage of DMF in Formulation A is 74% of the total weight of the sugar sphere and the DMF layer. The weight percentage of the enteric coating in Formulation A is 12% of the total weight of the sugar sphere and the DMF layer. The weight percentage of the functional coating in Formulation A is 4.5% of the total weight of the sugar sphere and DMF layer.

Example 2. In Vitro Dissolution Profiles

The in vitro dissolution profiles of the present pharmaceutical composition were determined according to methods described below, which are standard procedures published by USP-NF using USP apparatus II and IV.

Test 1.

The pharmaceutical compositions of the present invention were subjected to an in vitro dissolution test employing 0.1 N hydrochloric acid as dissolution medium during the first 2 hours of the test and then USP Simulated Intestinal Fluid (SIF) without pancreatin as dissolution medium in a USP Apparatus II (paddle apparatus).

Test 2.

The pharmaceutical compositions of the present invention were subjected to an in vitro dissolution test employing USP Simulated Gastric Fluid (SGF) without pepsin as dissolution medium during the first 2 hours of the test and then USP Simularted Intestinal Fluid (SIF) without pancreatin as dissolution medium in a USP Apparatus IV (flow-through cell).

Test 3.

The pharmaceutical compositions of the present invention were subjected to an in vitro dissolution test employing USP Simularted Intestinal Fluid (SIF) without pancreatin as dissolution medium in a USP Apparatus IV (flow-through cell).

USP SIF solution can be prepared according to according to procedures described in USP35-NF30. For 1 L scale, the SIF solution can be prepared by dissolving 6.8 g of monobasic potassium phosphate in 250 mL of water followed by mixing. 77 mL of 0.2 N sodium hydroxide and 500 mL of water are added sequentially. The pH of the resulting solution is adjusted with either 0.2 N sodium hydroxide or 0.2 N hydrochloric acid to a pH of 6.8±0.1 followed by dilution with water to 1000 mL. USP SGF solution can be prepared according to procedures described in USP35-NF30. For 1 L scale, the SGF solution can be prepared by dissolving 2.0 g of sodium chloride (NaCl) in 7.0 mL of hydrochloric acid (HCl) and sufficient water to make 1000 mL.

Figure 2:
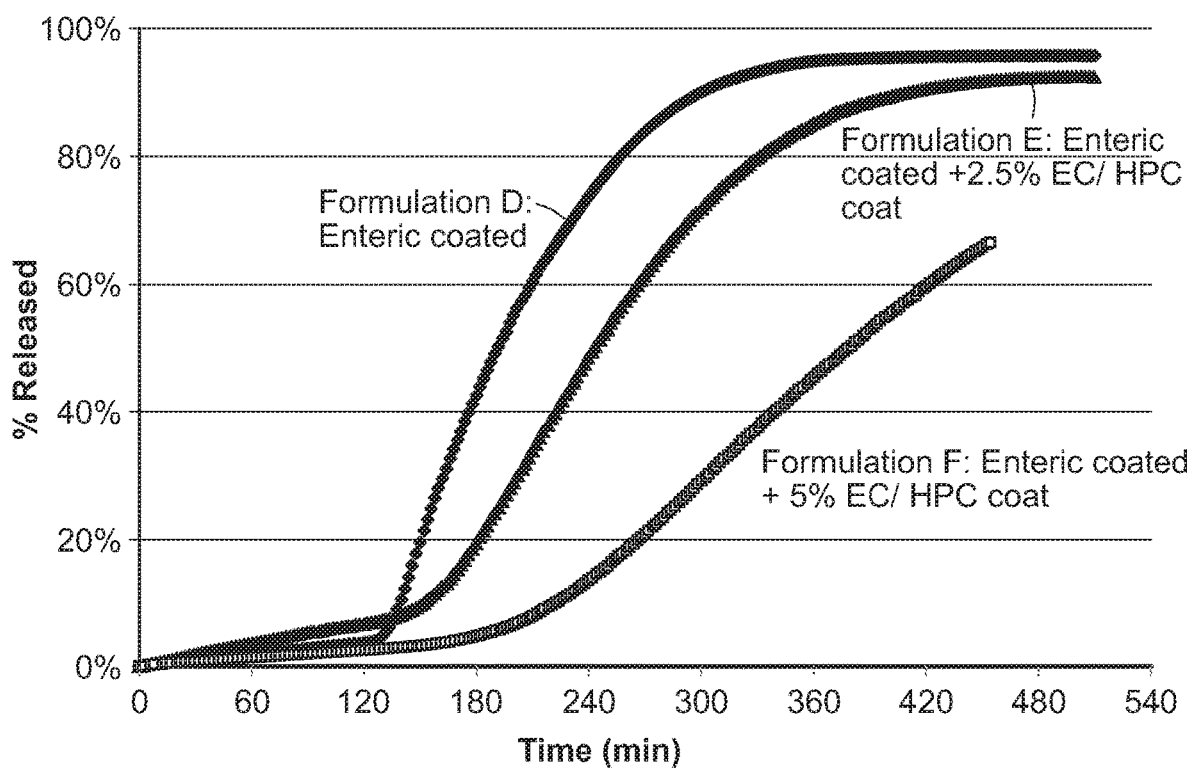
FIG. 2. shows in vitro dissolution profiles for formulations D, E and F of the present invention using dissolution test 2.
Figure 3:
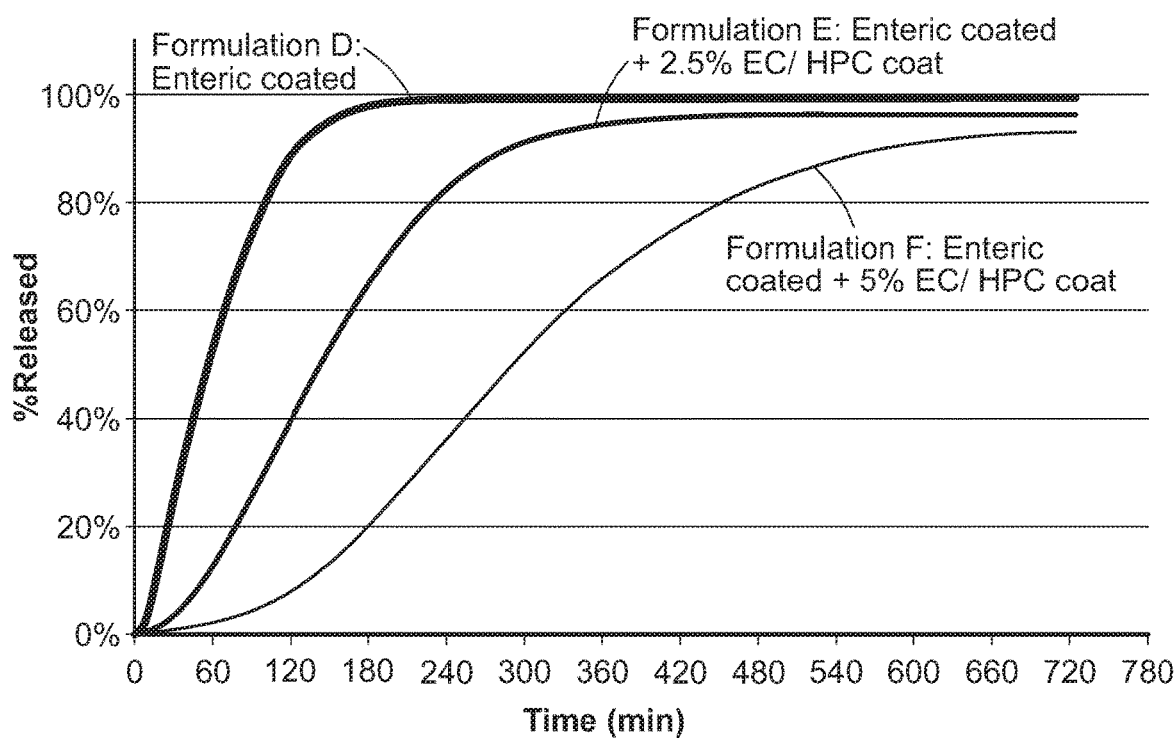
FIG. 3. shows in vitro dissolution profiles for formulations D, E and F of the present invention using dissolution test 3.
Figure 12:
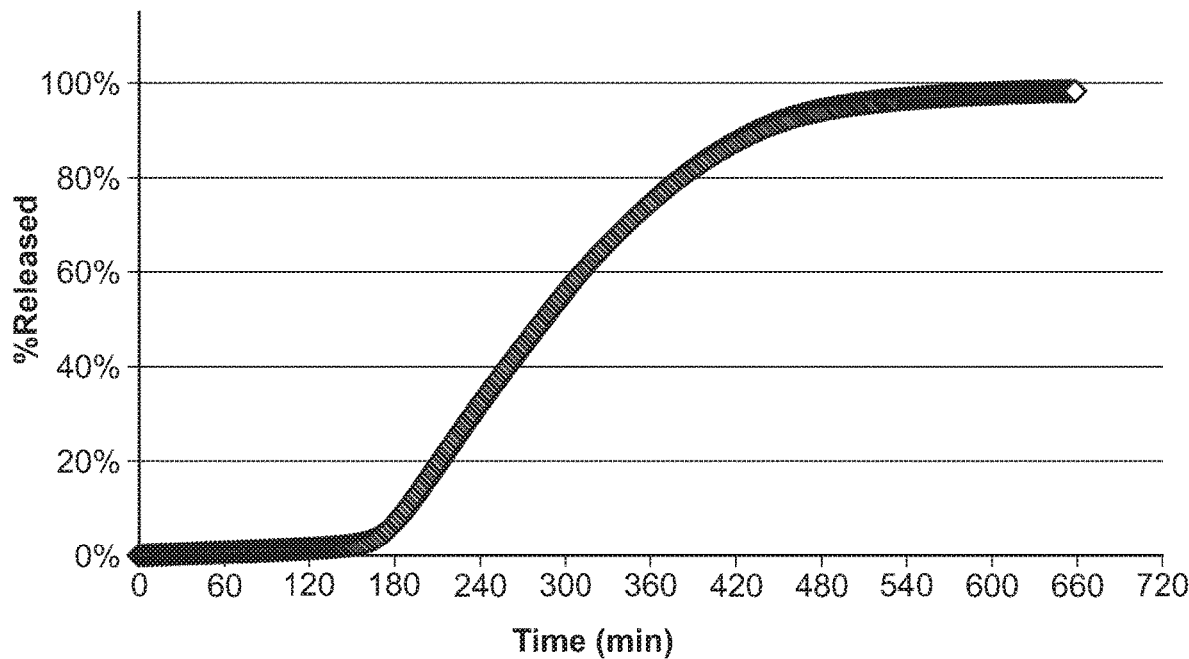
FIG. 12 shows in vitro dissolution profiles for bead formulations with various amounts of functional coatings (EC/HPC 60:40) using dissolution test 2.
Figure 13:
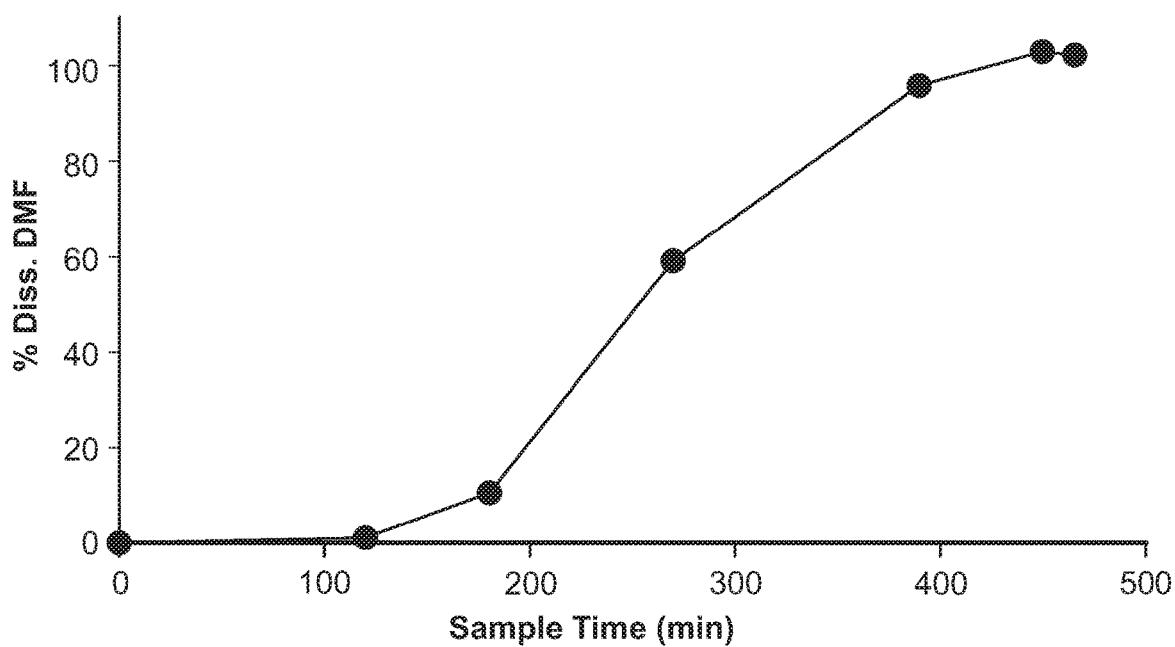
FIG. 13 shows in vitro dissolution profiles for bead formulations with various amounts of functional coatings (EC/HPC 60:40) using dissolution test 1.

The dissolution profiles for various bead formulations with and without functional coatings were determined. The dissolution profiles for Formulations D, E and F are shown in FIG. 1 (using Test 1), FIG. 2 (using Test 2) and FIG. 3 (using Test 3). The dissolution profiles for Formulation A are shown in FIG. 12 (using Test 2) and FIG. 13 (using Test 1).

Figure 4:
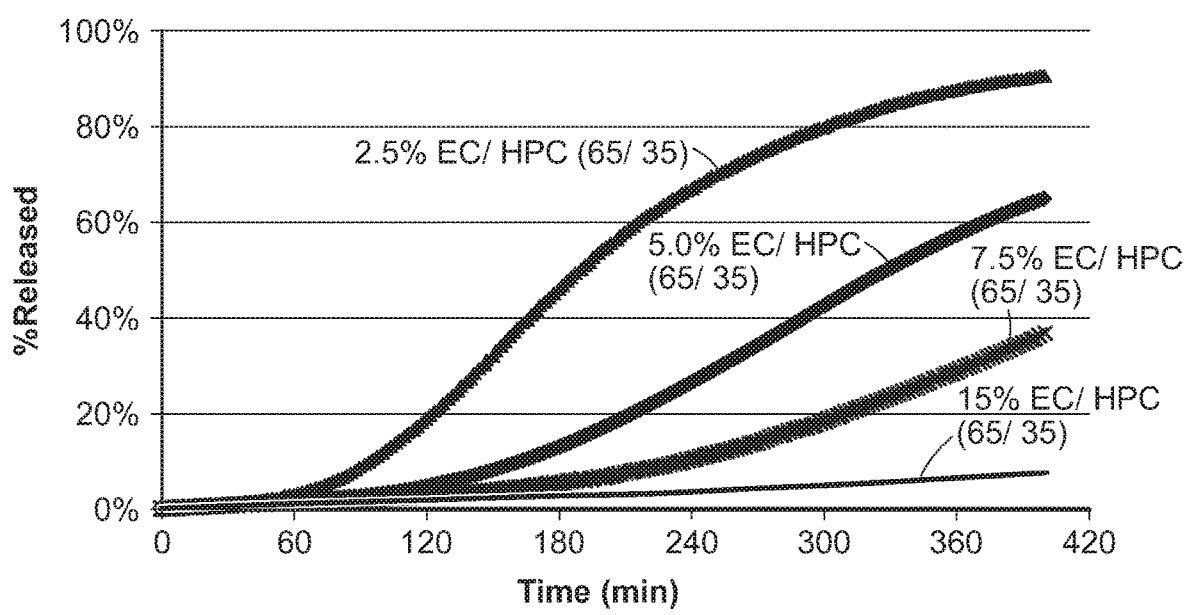
FIG. 4 shows in vitro dissolution profiles for bead formulations with various amounts of functional coatings (EC/HPC 65:35) using dissolution test 3.
Figure 5:
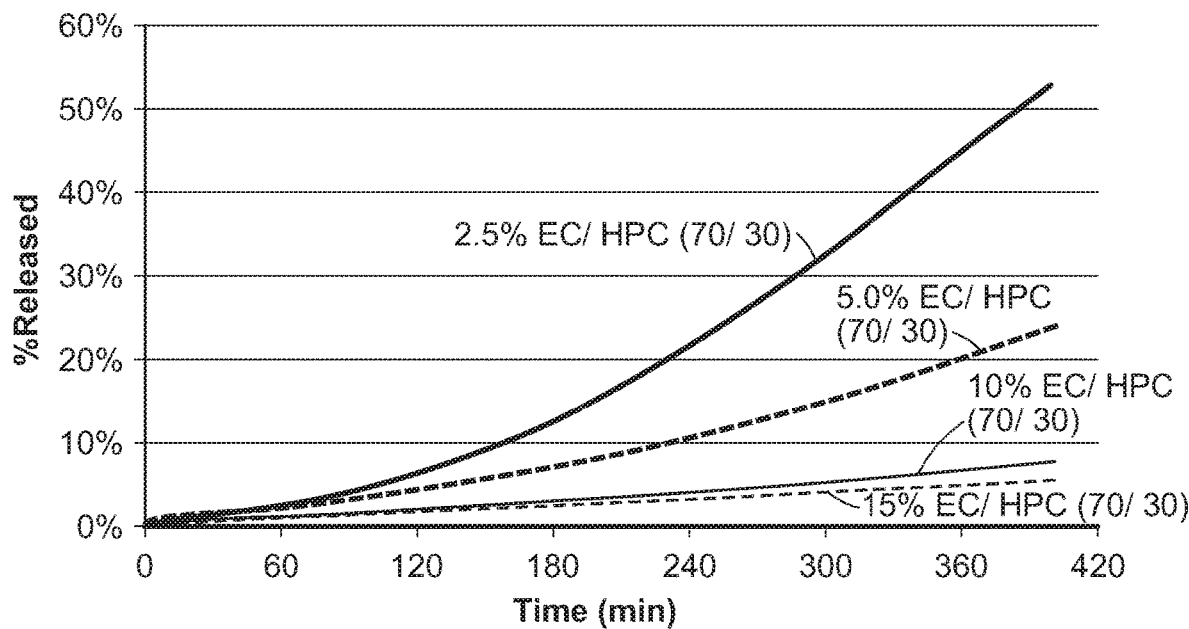
FIG. 5 shows in vitro dissolution profiles for bead formulations with various amounts of functional coatings (EC/HPC 70:30) using dissolution test 3.

The dissolution profiles for additional bead formulations having EC/HPC functional coatings are shown in FIG. 4 (using Test 2) and FIG. 5 (using Test 3). All the formulations having functional coating show extended release in vitro dissolution profiles; while the formulation without any functional coating release DMF significantly faster than those with functional coatings.

Figure 6:
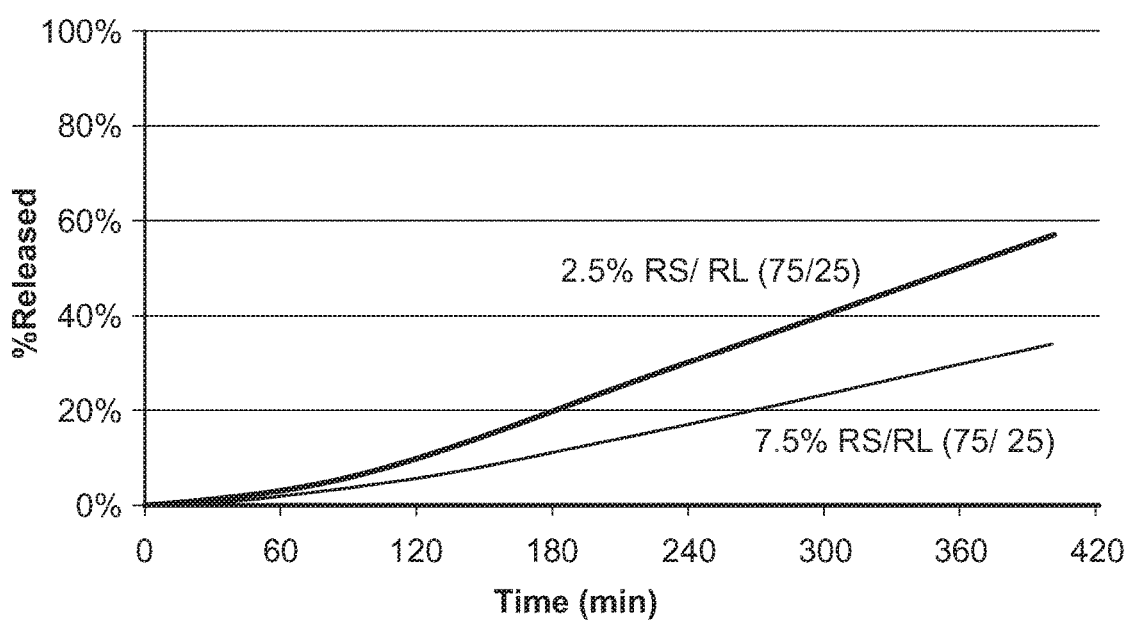
FIG. 6 shows in vitro dissolution profiles for bead formulations with various amounts of functional coatings (Eudragit RS/RL 75:25) using dissolution test 3.
Figure 7:
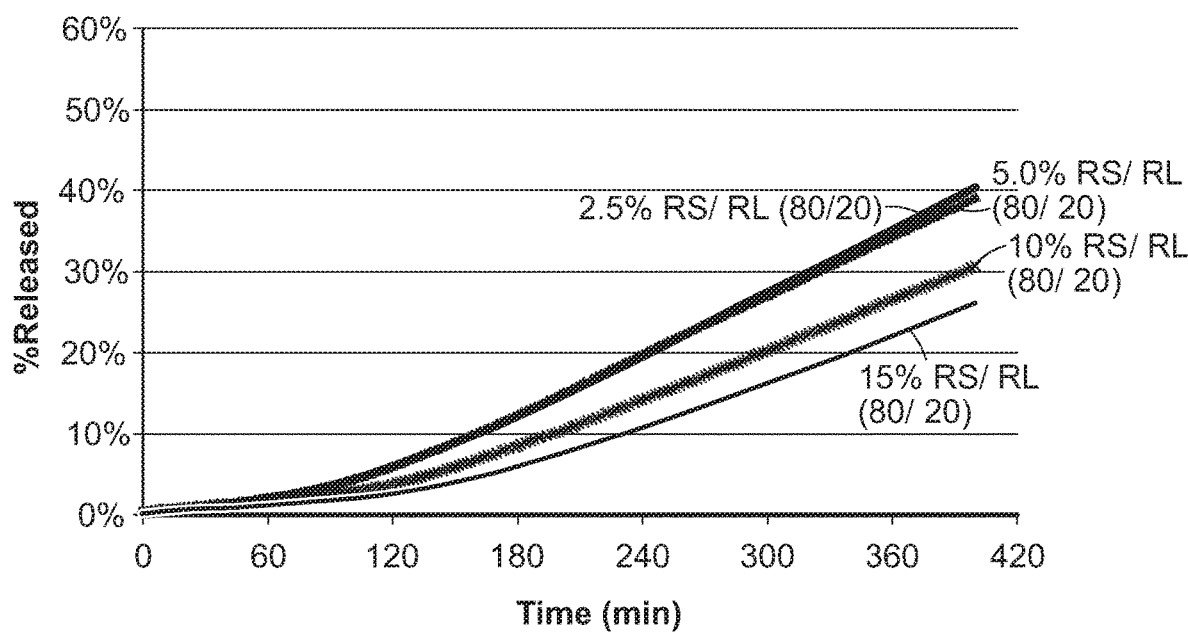
FIG. 7 shows in vitro dissolution profiles for bead formulations with various amounts of functional coatings (Eudragit RS/RL 80:20) using dissolution test 3.

Bead formulations with various amount of Eudragit RS/RL as functional coatings also exhibit extended release dissolution profiles, as shown in FIG. 6 (using Test 2) and FIG. 7 (using Test 2).

Example 3. In Vivo Pharmacokinetic Profiles

Formulations D, E and F with different release profile were selected for a dog PK study.

Male dogs were divided into six test groups and 1 control group with 4 dogs in each group. Dogs in the control group were administered with currently approved Tecfidera® formulation. Dogs in the test groups were administered with Formulations D, E or F or other DMF formulations. Dogs were fasted overnight until 1 hour post dose. 240 mg DMF in size 0 capsules were administered to the dogs orally, followed by approximately 10 mL of water. A second flush with approximately 10 mL of water may be administered if necessary to ensure capsule delivery.

Approximately 1 mL of blood was collected from each animal at 10 blood collection time points: predose and at 0.25, 0.5, 1, 2, 4, 8, 12, 16, and 24 hours postdose. Blood was collected via a jugular vein into tubes containing sodium heparin anticoagulant. Prior to blood collection, 40 µL of 250 mg/mL solution of aqueous sodium fluoride was added to each collection tube. The NaF solution may be prepared on the day prior to the study and stored refrigerated between uses and equilibrated to ambient temperature and vortexed prior to each use. The cephalic vein may be used as an alternative blood collection site.

At each protocol specified time point, 1 mL of blood was collected into a chilled sodium heparin/sodium fluoride tube and mixed immediately by gently inverting the tube 5 to 7 times to ensure uniform mixing. Avoid vigorous shaking to prevent hemolysis of the blood sample. Place the blood sample into wet ice or cryorack. Centrifuge samples within 30 minutes of collection at 4° C. for 15 minutes at 1500×g. Plasma was aliquoted equally into 1.8 or 2 mL cryovials and be maintained on dry ice prior to storage at approximately −70° C.

Plasma was then analyzed. MMF in the plasma was quantified by LC-MS/MS with calibration range of 10 ng/ml-5000 ng/ml using $^{13}$C-MMF as internal standard. Plasma can be diluted with 1:10 dilution if necessary.

Figure 8:
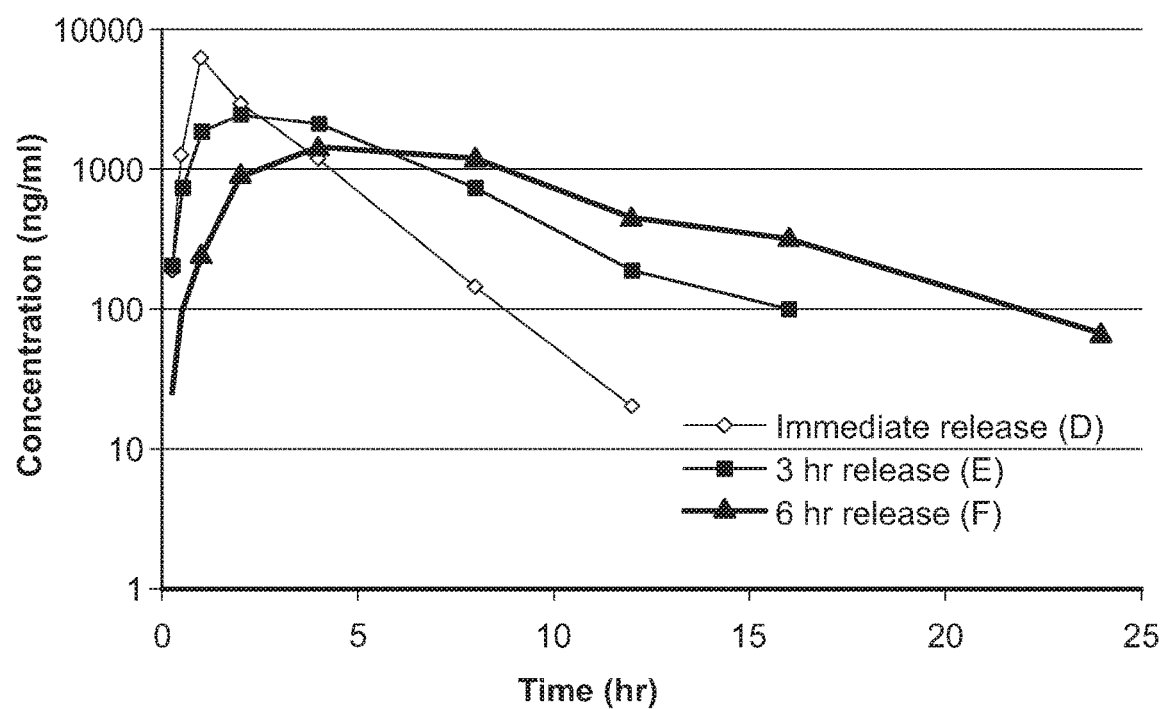
FIG. 8 shows in vivo pharmacokinetic profile of formulations D, E and F in a dog PK study.
Figure 9:
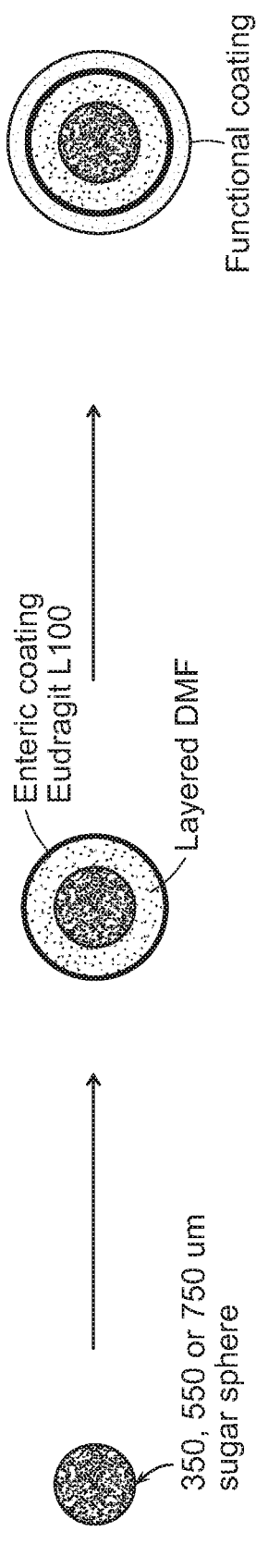
FIG. 9 shows exemplary scheme for preparing bead formulations of the present invention using fluid bed coating method.
Figure 10:
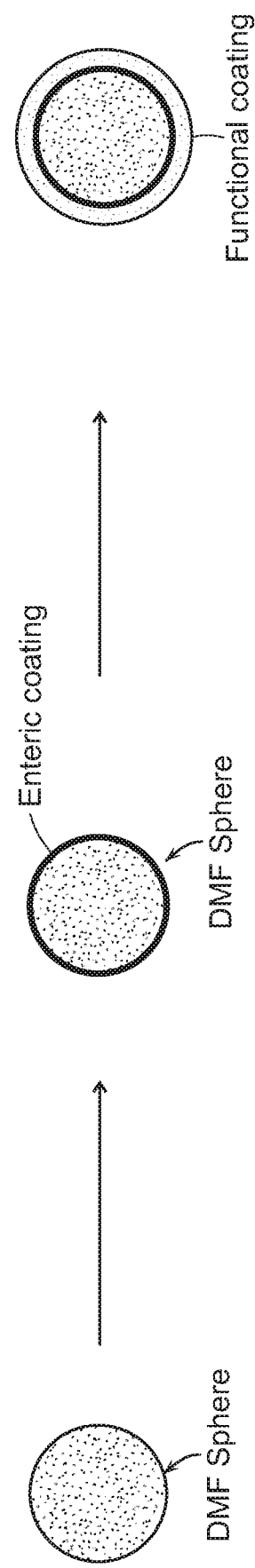
FIG. 10 shows exemplary scheme for preparing bead formulations of the present invention using extrusion spheronization method.
Figure 11:
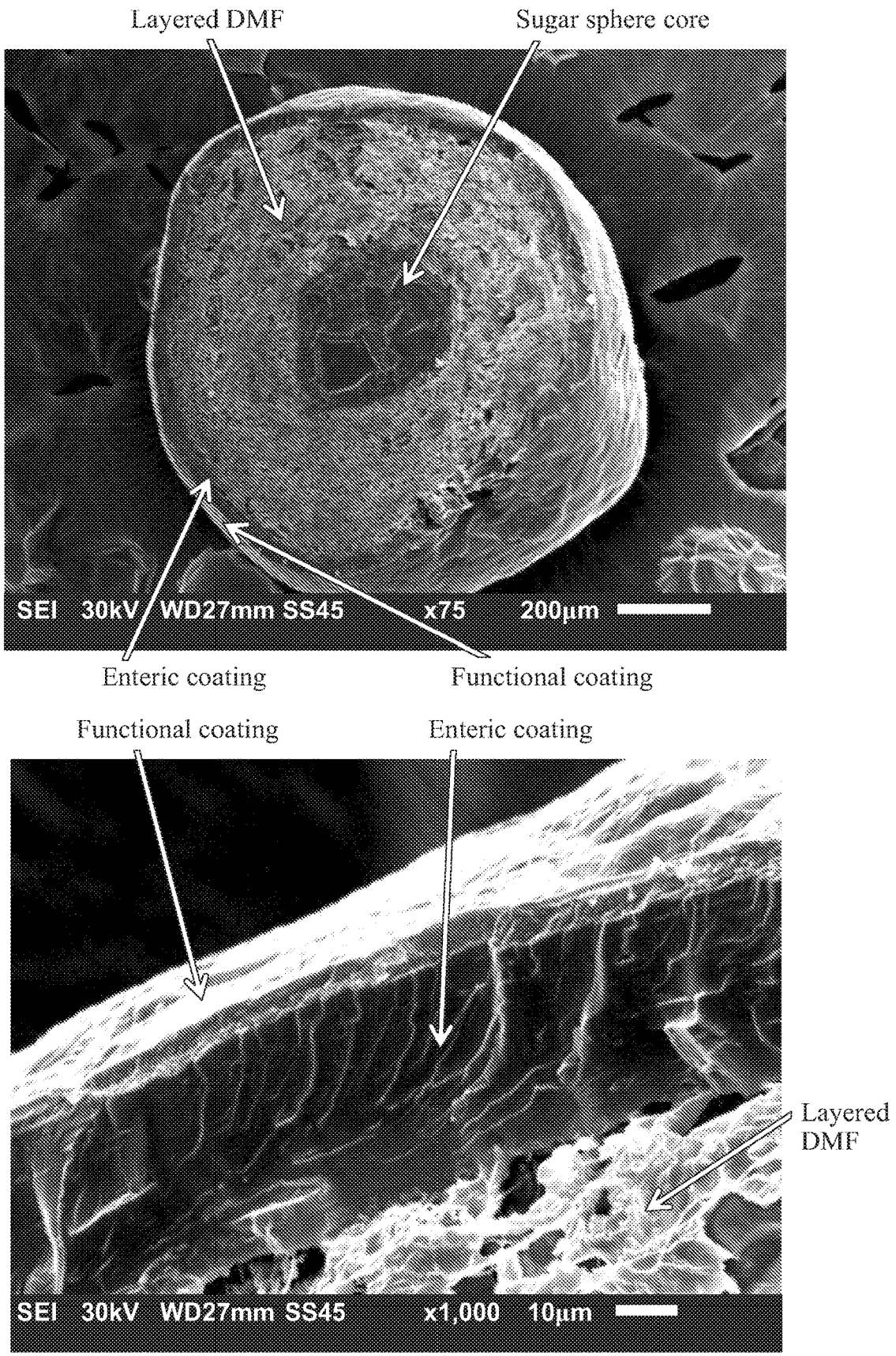
FIG. 11 shows SEM images of extended release DMF layered bead formulation of the present invention.

As shown in FIG. 8 and Table 7 below, all three formulations have very similar AUC. The plasma profile of formulation F extends to later hours than formulation E and formulation D. This is consistent with the fact that the release time for formulation F>formulation E>formulation D.

TABLE 7

AUC, $C_{max}$, $t_{max}$ and $t_{1/2}$ from the dog study

| formulation | $AUC_\infty/D$ [ng*h*kg/ml/mg] | | $C_{max}/D$ [kg*ng/ml/mg] | | $t_{max}$ [hr] | | $t_{1/2}$ [hr] | |
|---|---|---|---|---|---|---|---|---|
| | mean | stdev | mean | stdev | mean | stdev | mean | stdev |
| Formulation D | 644 | 78 | 186 | 63 | 1.5 | 0.7 | 1.2 | 0.1 |
| Formulation E | 722 | 211 | 121 | 33 | 2.5 | 1.0 | 2.2 | 1.2 |
| Formulation F | 784 | | 85 | | 4.0 | | 3.0 | |

Example 4. Methods of Preparing Beads Formulation by Extrusion Spheronization

Alternatively, the beads formulation can be prepared using extrusion spheronization. DMF is first mixed with excipients and solvent into a wet mass. The wet mass is then forced through an extruder to form cylindrical pellets. The diameter of the pellets ranges from 0.6 mm to 2 mm depending on the equipment setting. The extruded pellets will then be spheronized in a spheronizer with a rotating disk. The diameter of the spheres can range from 0.6 to 2 mm depending on the initial cylindrical pellet size. Tables 8 and 9 below list exemplary formulations.

TABLE 8

Exemplary Formulations for Extrusion Spheronization

| DMF | 65% | 65% |
|---|---|---|
| Microcrystalline cellulose (Avicel PH101) | 11% | / |
| Microcrystalline cellulose (Avicel PH102) | / | 15% |
| Lactose Monohydrate Fast Flo | / | 10% |
| Starch 1500 | 4% | / |
| Ac-Di-Sol | 10% | 10% |
| PEO | 10% | / |
| PEO 4000 | / | / |

TABLE 9

Exemplary Formulations for Extrusion Spheronization

| DMF | 75% | 75% |
|---|---|---|
| Microcrystalline Cellulose (Avicel PH101) | 14% | 14% |
| Starch 1500 | 4% | 4% |
| Ac-Di-Sol | 5% | |
| Explotab | | 5% |
| TEC | 2% | 2% |

The DMF spheres are then coated with the enteric coating and the functional coating described above.

Example 5. Methods of Preparing Bead Formulations by Fluid Bed Spheronization

The bead formulations of the present invention can also be prepared utilizing the Glatt's CPS unit to spheronize dimethyl fumarate and excipients (MCC and disintegrant) with solvents (water, ethenol or API) into spheres with size ranging from 500 um to 1.5 mm.

We claim:
1. A pharmaceutical composition in the form of a bead comprising:
an inert core;
a first layer surrounding the inert core, wherein the first layer comprises dimethyl fumarate;
wherein the weight percentage of dimethyl fumarate is 40%-80% of the total weight of the inert core and the first layer;
an enteric coating surrounding the first layer; wherein the weight percentage of the enteric coating is 1-20% of the total weight of the inert core and the first layer; and
an extended release functional coating surrounding the enteric coating, wherein
the functional coating comprises a mixture of ethylcellulose (EC) and hydroxypropyl cellulose (HPC), wherein the weight ratio of ethylcellulose to hydroxypropyl cellulose is between 80:20 and 50:50; or
the functional coating comprises a mixture of poly (ethyl acrylate-co-methyl methacrylate-co-trimethylammonioethyl methacrylate chloride) 1:2:0.1 and poly(ethyl acrylate-co-methyl methacrylate-co-trimetylammonioethyl methacrylate chloride) 1:2:0.2, wherein the weight ratio of poly(ethyl acrylate-co-methyl methacrylate-co-trimethylammonioethyl methacrylate chloride) 1:2:0.1 and poly(ethyl acrylate-co-methyl methacrylate-co-trimethylammonioethyl methacrylate chloride) 1:2:0.2 is 90:10 to 60:40;
wherein the weight percentage of the functional coating is 1-30% of the total weight of the inert core and the first layer.

2. The pharmaceutical composition of claim 1, wherein the enteric coating comprises an excipient selected from the group consisting of a copolymer of methacrylic acid and methyl methacrylate, a copolymer of methacrylic acid and ethyl acrylate, hypromellose phthalate (HPMCP), cellulose acetate phthalate.

3. The pharmaceutical composition of claim 2, wherein the enteric coating comprises a copolymer of methacrylic acid and methyl methacrylate.

4. The pharmaceutical composition of claim 3, wherein the ratio of the methacrylic acid to the methyl methacrylate in the copolymer is 0.8:1 to 1.2:1.

5. The pharmaceutical composition of claim 1, wherein the functional coating comprises a mixture of ethylcellulose (EC) and hydroxypropyl cellulose (HPC).

6. The pharmaceutical composition of claim 5, wherein the weight ratio of ethylcellulose to hydroxypropyl cellulose is between 75:25 and 60:40.

7. The pharmaceutical composition of claim 5, wherein the weight ratio of ethylcellulose to hydroxypropyl cellulose is 70:30, 65:35 or 60:40.

8. The pharmaceutical composition of claim 1, wherein the functional coating comprises a mixture of poly(ethyl acrylate-co-methyl methacrylate-co-trimethylammonioethyl methacrylate chloride) 1:2:0.1 and poly(ethyl acrylate-co-methyl methacrylate-co-trimetylammonioethyl methacrylate chloride) 1:2:0.2.

9. The pharmaceutical composition of claim 1, wherein the pharmaceutical composition comprises:
(i) an inert core;
a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 2.0%-3.0% of the total weight of the inert core and the first layer,
wherein the weight percentage of the inert core is 20-24% of the total weight of the inert core and the first layer;
(ii) an inert core;
a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 4.5%-5.5% of the total weight of the inert core and the first layer,
wherein the weight percentage of the inert core is 20-24% of the total weight of the inert core and the first layer;
(iii) an inert core;
a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 5.0%-6.0% of the total weight of the inert core and the first layer,
wherein the weight percentage of the inert core is 20-24% of the total weight of the inert core and the first layer;
(iv) an inert core;
a first layer surrounding the inert core, wherein the first layer comprises dimethyl fumarate and a binder and wherein the weight percentage of dimethyl fumarate is 68%-72% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 11.5%-12.5% of the total weight of the inert core and the first layer,
wherein the weight percentage of the inert core is 20-24% of the total weight of the inert core and the first layer; or
(v) an inert core;
a first layer surrounding the inert core, wherein the first layer comprises dimethyl fumarate and a binder and wherein the weight percentage of dimethyl fumarate is 72%-76% of the total weight of the inert core and the first layer and the weight percentage of the binder is 5-10% of the total weight of the inert core and the first layer;
an enteric coating surrounding the first layer, wherein the weight percentage of the enteric coating is 11-13% of the total weight of the inert core and the first layer; and
a functional coating surrounding the enteric coating, wherein the weight percentage of the functional coating is 4.0%-5.0% of the total weight of the inert core and the first layer,
wherein the weight percentage of the inert core is 20-24% of the total weight of the inert core and the first layer.

10. The pharmaceutical composition of claim 9, wherein the inert core comprises sucrose or starch; the binder is HPMC; the enteric coating comprises a copolymer of methacrylic acid and methyl methacrylate and the ratio of methacrylic acid to methyl methacrylate is 1:1; and the functional coating comprises of a mixture of ethylcellulose (EC) and hydroxypropyl cellulose (HPC) and the weight ratio of ethylcellulose (EC) to hydroxypropyl cellulose (HPC) is 65:35.

11. The pharmaceutical composition of claim 10, wherein the enteric coating further comprises triethyl citrate and the weight ratio of the copolymer of methacrylic acid and methyl methacrylate to triethyl citrate is 5:1; and the functional coating comprises a mixture of ethylcellulose polymer and hydroxypropyl cellulose polymer, wherein the ethylcellulose polymer has a viscosity in the range of 9-11 cP for 5% weight solution in 80% toluene and 20% ethanol; the hydroxypropyl cellulose polymer has a viscosity in the range of 150-400 cP for 5% by weight solution in water; and the weight ratio of the ethylcellulose polymer to the hydroxypropyl cellulose polymer is 65:35.

12. The pharmaceutical composition of claim 9, wherein the inert core comprises sucrose or starch; the binder is HPMC; the enteric coating comprises a copolymer of methacrylic acid and methyl methacrylate and the ratio of methacrylic acid to methyl methacrylate is 1:1; and the functional coating comprises of a mixture of ethylcellulose (EC) and hydroxypropyl cellulose (HPC) and the weight ratio of ethylcellulose (EC) to hydroxypropyl cellulose (HPC) is 60:40.

13. The pharmaceutical composition of claim 12, wherein the enteric coating further comprises triethyl citrate and the weight ratio of the copolymer of methacrylic acid and methyl methacrylate to triethyl citrate is 5:1; and the functional coating comprises a mixture of ethylcellulose polymer and hydroxypropyl cellulose polymer, wherein the ethylcellulose polymer has a viscosity in the range of 9-11 cP for 5% weight solution in 80% toluene and 20% ethanol; the hydroxypropyl cellulose polymer has a viscosity in the range of 150-400 cP for 5% by weight solution in water; and the weight ratio of the ethylcellulose polymer to the hydroxypropyl cellulose polymer is 60:40.

14. A pharmaceutical composition in the form of a bead comprising:
- a core comprising dimethyl fumarate; wherein the weight percentage of dimethyl fumarate is 40%-80% of the total weight of the core;
- an enteric coating surrounding the core; wherein the weight percentage of the enteric coating is 1-20% of the total weight of the core; and
- an extended release functional coating surrounding the enteric coating, wherein
- the functional coating comprises a mixture of ethylcellulose (EC) and hydroxypropyl cellulose (HPC), wherein the weight ratio of ethylcellulose to hydroxypropyl cellulose is between 80:20 and 50:50; or
- the functional coating comprises a mixture of poly(ethyl acrylate-co-methyl methacrylate-co-trimethylammonioethyl methacrylate chloride) 1:2:0.1 and poly(ethyl acrylate-co-methyl methacrylate-co-trimethylammonioethyl methacrylate chloride) 1:2:0.2, wherein the weight ratio of poly(ethyl acrylate-co-methyl methacrylate-co-trimethylammonioethyl methacrylate chloride) 1:2:0.1 and poly(ethyl acrylate-co-methyl methacrylate-co-trimetylammonioethyl methacrylate chloride) 1:2:0.2 is 90:10 to 60:40; wherein the weight percentage of the functional coating is 1-30% of the total weight of the core.

15. A pharmaceutical composition in the form of a bead with a diameter of 0.5-2 mm comprising:
- an inert core;
- a first layer surrounding the inert core, wherein the first layer comprises dimethyl fumarate;
- wherein the weight percentage of dimethyl fumarate is 40%-80% of the total weight of the inert core and the first layer;
- an extended release functional coating surrounding the first layer, wherein
- the functional coating comprises a mixture of ethylcellulose (EC) and hydroxypropyl cellulose (HPC), wherein the weight ratio of ethylcellulose to hydroxypropyl cellulose is between 80:20 and 50:50; or
- the functional coating comprises a mixture of poly(ethyl acrylate-co-methyl methacrylate-co-trimethylammonioethyl methacrylate chloride) 1:2:0.1 and poly(ethyl acrylate-co-methyl methacrylate-co-trimethylammonioethyl methacrylate chloride) 1:2:0.2, wherein the weight ratio of poly(ethyl acrylate-co-methyl methacrylate-co-trimethylammonioethyl methacrylate chloride) 1:2:0.1 and poly(ethyl acrylate-co-methyl methacrylate-co-trimetylammonioethyl methacrylate chloride) 1:2:0.2 is 90:10 to 60:40; wherein the weight percentage of the functional coating is 1-30% of the total weight of the inert core and the first layer; and
- an enteric coating surrounding the functional coating; wherein the weight percentage of the enteric coating is 1-20% of the total weight of the inert core and the first layer.

16. A pharmaceutical composition in the form of a bead with a diameter of 0.5-2 mm comprising:
- a core comprising dimethyl fumarate; wherein the weight percentage of dimethyl fumarate is 40%-80% of the total weight of the core;
- an extended release functional coating surrounding the core, wherein
- the functional coating comprises a mixture of ethylcellulose (EC) and hydroxypropyl cellulose (HPC), wherein the weight ratio of ethylcellulose to hydroxypropyl cellulose is between 80:20 and 50:50; or
- the functional coating comprises a mixture of poly(ethyl acrylate-co-methyl methacrylate-co-trimethylammonioethyl methacrylate chloride) 1:2:0.1 and poly(ethyl acrylate-co-methyl methacrylate-co-trimethylammonioethyl methacrylate chloride) 1:2:0.2, wherein the weight ratio of poly(ethyl acrylate-co-methyl methacrylate-co-trimethylammonioethyl methacrylate chloride) 1:2:0.1 and poly(ethyl acrylate-co-methyl methacrylate-co-trimetylammonioethyl methacrylate chloride) 1:2:0.2 is 90:10 to 60:40; wherein the weight percentage of the functional coating is 1-30% of the total weight of the core; and
- an enteric coating surrounding the functional coating; wherein the weight percentage of the enteric coating is 1-20% of the total weight of the core.

17. A method of treating a subject having multiple sclerosis comprising administering to the subject an effective amount of a pharmaceutical composition of claim 1.

18. A method of treating a subject having multiple sclerosis comprising administering to the subject an effective amount of a pharmaceutical composition of claim 14.

19. A method of treating a subject having multiple sclerosis comprising administering to the subject an effective amount of a pharmaceutical composition of claim 15.

20. A method of treating a subject having multiple sclerosis comprising administering to the subject an effective amount of a pharmaceutical composition of claim 16.

* * * * *